United States Patent
Tang et al.

(10) Patent No.: US 11,118,109 B2
(45) Date of Patent: Sep. 14, 2021

(54) ORGANIC LUMINOGENS

(71) Applicant: THE HONG KONG UNIVERSITY OF SCIENCE AND TECHNOLOGY, Hong Kong (CN)

(72) Inventors: Benzhong Tang, Hong Kong (CN); Jianguo Wang, Hong Kong (CN); Xinggui Gu, Hong Kong (CN); Pengfei Zhang, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 0 days.

(21) Appl. No.: 16/615,667

(22) PCT Filed: May 24, 2018

(86) PCT No.: PCT/CN2018/088189
§ 371 (c)(1),
(2) Date: Nov. 21, 2019

(87) PCT Pub. No.: WO2018/214932
PCT Pub. Date: Nov. 29, 2018

(65) Prior Publication Data
US 2020/0224090 A1 Jul. 16, 2020

Related U.S. Application Data

(60) Provisional application No. 62/603,333, filed on May 26, 2017, provisional application No. 62/710,681, filed on Feb. 26, 2018.

(51) Int. Cl.
| | |
|---|---|
| *C07D 263/32* | (2006.01) |
| *C07D 233/58* | (2006.01) |
| *C07D 277/22* | (2006.01) |
| *C09K 11/06* | (2006.01) |
| *A01N 43/76* | (2006.01) |
| *G01N 21/64* | (2006.01) |

(52) U.S. Cl.
CPC ............. *C09K 11/06* (2013.01); *A01N 43/76* (2013.01); *C07D 263/32* (2013.01); *G01N 21/6486* (2013.01); *C09K 2211/1018* (2013.01)

(58) Field of Classification Search
CPC ... C07D 263/32; C07D 233/58; C07D 277/22
See application file for complete search history.

(56) References Cited

U.S. PATENT DOCUMENTS

2012/0095180 A1 4/2012 Bertrand et al.

FOREIGN PATENT DOCUMENTS

| DE | 253818 A1 | * | 2/1988 |
|---|---|---|---|
| DE | 254003 A1 | | 2/1988 |
| WO | 2011003029 A2 | | 1/2011 |
| WO | 2015033313 A3 | | 3/2015 |
| WO | WO-2015/033313 A2 | * | 3/2015 |
| WO | 2016026122 A1 | | 2/2016 |

OTHER PUBLICATIONS

Chemical Abstracts Registry No. 54902-05-5, indexed in the Registry file on STN CAS Online Nov. 16, 1984. (Year: 1984).*
Moschny et al., Helvetica Chimica Acta (1999), 82(11), pp. 1981-1993. (Year: 1999).*
A machine generated English translation of DD 254003 A1 (Hartmann et al.), 1988. (Year: 1988).*
Shvaika et al., Zhurnal Organicheskoi Khimii (1974), 10(11), pp. 2429-2436. (Year: 1974).*
Chemical Abstracts Registry No. 2159088-32-9, indexed in the Registry file on STN CAS Online Dec. 15, 2017. (Year: 2017).*
A machine generated English translation of DD 253,818 A1, (Hartmann et al.), 1988. (Year: 1988).*
Shvaika et al., Recyclization reactions of heterocycles XVIII. Synthesis and recyclization of thiazolium and benzothiazolium salts. Chemistry of Heterocyclic Compounds, 12, 533-537 (1976). https://doi.org/10.1007/BF00470106. (Year: 1976).*
International Search Report dated Aug. 27, 2018 for PCT/CN2018/088189 (in English) Forms PCT/ISA/220, 210 and 237.

* cited by examiner

*Primary Examiner* — Laura L Stockton
(74) *Attorney, Agent, or Firm* — Nath, Goldberg & Meyer; Joshua B. Goldberg

(57) ABSTRACT

Small molecule compounds having aggregation-induced emission (AIE) characteristics. The compounds include organic, aromatic salts having anion-π⁺ interactions. In some embodiments, the anion-π⁺ interactions can include heavy-atom-anion-π⁺ interactions. The heavy atom anions can include bromine or iodide, for example. The compounds can be water-soluble. The compounds can be useful as probes for bioimaging, as room temperature luminogens for electroluminescent devices, and white organic light-emitting applications.

11 Claims, 26 Drawing Sheets

ORGANIC LUMINOGENS

FIELD

The present subject matter relates generally to a series of compounds with aggregation-induced emission characteristics and their applications in bioimaging, electroluminescent devices, and/or 3D printing.

BACKGROUND

Organic luminogens are useful in a variety of applications, including electroluminescent devices, optoelectronic devices, chemical sensors, and biological sensors, for example. However, the application of traditional organic luminogens is greatly limited by the aggregation caused quenching (ACQ) effect. Traditional organic luminogens are highly emissive in dilute solution, but become weakly emissive or non-emissive in high concentration solution when aggregated or in the solid state. Since the ACQ effect is harmful to practical applications, numerous steps were taken to prevent traditional luminogens from aggregating, including chemical reactions, physical methods and/or engineering processes. Unfortunately, these methods met with limited success.

In 2001, a group of propeller-shaped luminogens which are non-emissive in the solution state, but highly emissive in the aggregation or solid state, were introduced. This phenomenon was named aggregation induced emission (AIE). Since then, AIE cores such as silole, tetraphenylethylene (TPE) and tetraphenylpyrazine (TPP) have been developed. Based on these AIE cores, many AIE luminogens (AIEgens) with versatile functionalities and diverse applications were constructed. However, prior AIEgens have certain limitations, particularly with respect to mechanism of action and application. For example, many AIEgens based on silole, TPE and TPP cores are neutral molecules bearing neither negative charges nor positive charges. As such, these compounds can exhibit poor solubility in aqueous solutions, which can limit their application as chemical and biological probes. Although some extent of water solubility can be obtained by structure modification, the required synthetic process for such a modification may be tedious and time-consuming. Based on the above-mentioned aspects, new AIE cores which are photostable and can be easily prepared and functionalized are highly desirable.

Luminogens with room temperature phosphorescence (RTP) have attracted much interest in recent years due to the long-lived triplet manifold, which makes RTP luminogens more efficient than fluorescent counterparts in electroluminescent devices. In addition, RTP luminogens, as contrast agents, can exclude interference from cellular auto-fluorescence with a short lifetime to better monitor various cellular phenomena. RTP luminogens also have applications in biological hypoxia imaging, temperature, moisture and ion sensing, document security, and optical recording due to the selectivity of triplet excitons to oxygen, temperature and water. At present, RTP phosphors are usually confined to inorganics or organometallic complexes, which are expensive, suffer from poor processability, and are toxic and harmful to the environment. Pure organic RTP phosphors are more desirable because of their low cost, versatile molecular design, facile functionalization, and good processability.

In the past, pure organic luminogens have been very difficult to obtain. This is because such luminogens can have inefficient spin-orbit coupling (SOC) and fast nonradiative decay. Up to now, only a few kinds of pure organic luminogens have been developed, and mainly include keto, carbazole and borate systems, which are all covalent compounds.

Lighting accounts for about 12% of energy consumption in an average household. That percentage is up to 30% for commercial buildings; hence the exploration of efficient lighting devices is very necessary to save energy. White organic light-emitting luminogens have higher energy conversion efficiency, longer lifetime, and lower heat value than those providing single-color emission. Most white organic light-emitting materials reported so far generally include a combination of multi-components with two complementary colors (blue and yellow) or three primary colors (blue, green, and red). Compared to these multi-component emitters, organic single-molecule white light emitters (OSMWLEs) exhibit superior performance, such as no phase segregation, no color aging, good reproducibility, improved stability, and simple device fabrication procedure. In the past, however, development of OSMWLEs or a single molecule with two appropriate emissions has met with many challenges.

At present, according to the origin of two emission bands, OSMWLEs can be divided into three classes including (1) pure fluorescent OSMWLEs, such as monomer/excimer systems, excited-state intramolecular proton transfer systems, prompt/delayed fluorescence systems, and conformation-dependent emission systems; (2) hybrid fluorescent and phosphorescent OSMWLEs; and (3) pure phosphorescent OSMWLEs. OSMWLEs based on phosphorescent emitter are the least populated class owing to the limit of RTP luminogens. Thus, a new strategy is urgently needed for preparing RTP materials for OSMWLEs application.

Accordingly, organic luminogens overcoming these challenges are highly desirable.

SUMMARY

The present subject matter contemplates small molecule compounds having aggregation-induced emission (AIE) characteristics. The present compounds include organic, aromatic salts having anion-$\pi^+$ interactions. In some embodiments, the anion-$\pi^+$ interactions can include heavy-atom-anion-$\pi^+$ interactions. The heavy atom anions can include bromine or iodide, for example.

The compounds can be water-soluble. The compounds can be useful as probes for bioimaging, as room temperature luminogens for electroluminescent devices, and/or in white organic light-emitting applications.

In an embodiment, the compounds have a backbone structural formula selected from the group consisting of:

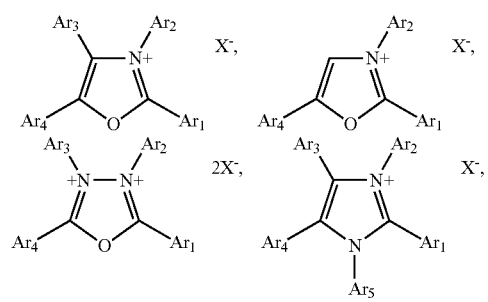

-continued

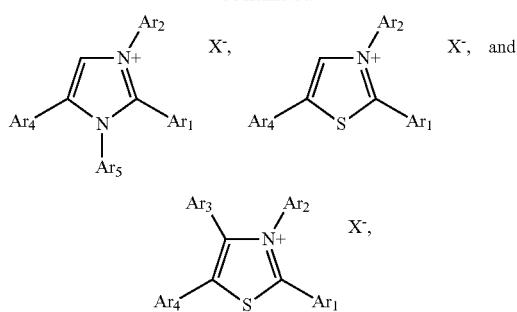

wherein each of Ar₁, Ar₂, Ar₃, Ar₄, and Ar₅ is independently an aryl, heteroaryl, or heterocyclic group, the aryl, heteroaryl, or heterocyclic group being unsubstituted or substituted with one or more substituents selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, alkoxy group,

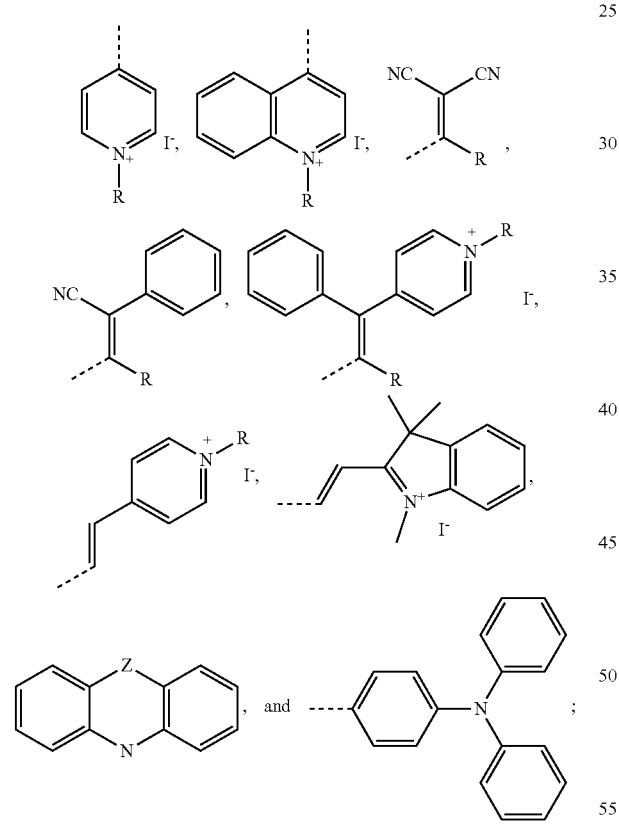

wherein $X^-$ is selected from the group consisting of $PF_6^-$, $BF_4^-$, $SbF_5^-$, $CH_3COO^-$, $CF_3COO^-$, $CO_3^{2-}$, $SO_4^{2-}$, $SO_3^{2-}$, $CF_3SO_2^-$, $TSO^-$, $ClO_4^-$, $F^-$, $Cl^-$, $Br^-$, $I^-$, $(F_3CSO_2)N^-$, and $PO_4^{3-}$;

wherein R is selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, alkoxy group; and wherein Z is C, N, O, or S, provided that when the backbone structural formula is

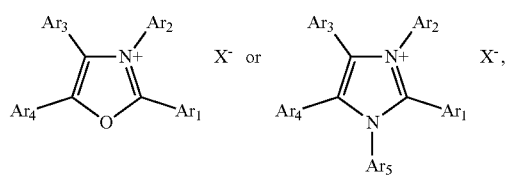

at least one of Ar₂, Ar₃, and Ar₄ is other than unsubstituted phenyl.

In a further embodiment, the compounds have a backbone structural formula selected from:

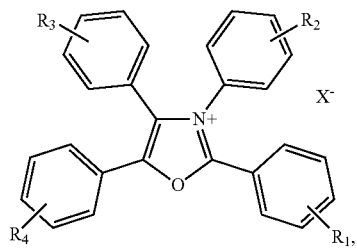

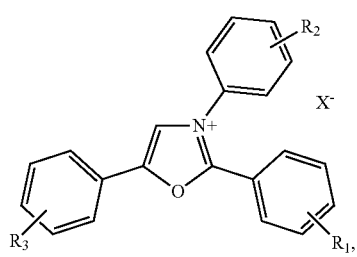

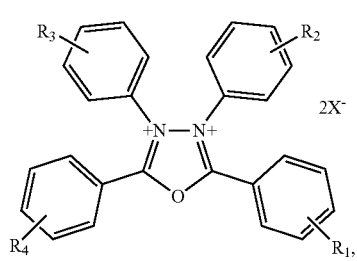

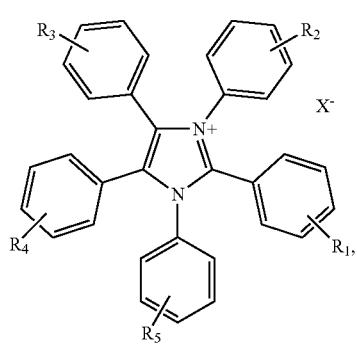

-continued

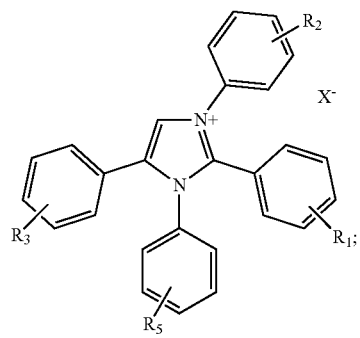

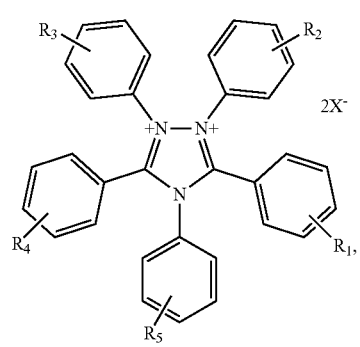

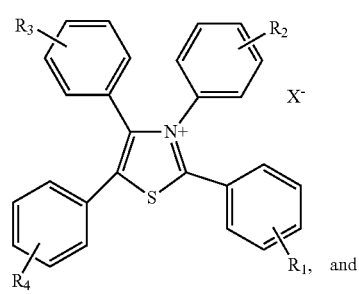

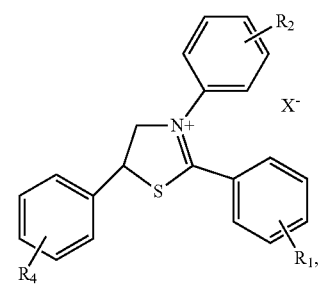

wherein each of $R_1$, $R_2$, $R_3$, $R_4$, and $R_5$ is independently selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, alkoxy group,

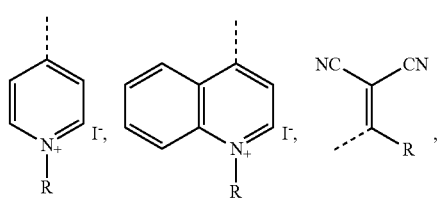

-continued

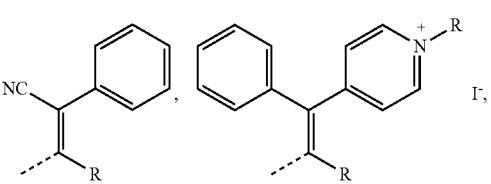

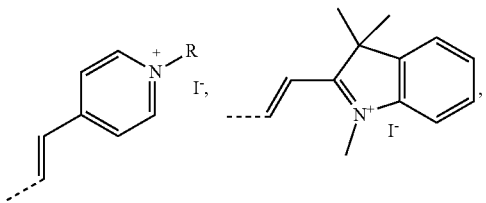

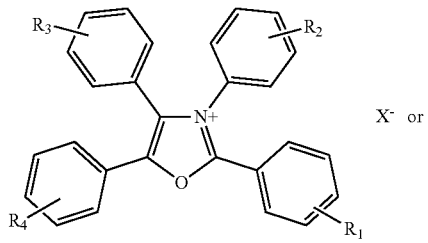

wherein X is selected from the group consisting of $PF_6^-$, $BF_4^-$, $SbF_5^-$, $CH_3COO^-$, $CF_3COO^-$, $CO_3^{2-}$, $SO_4^{2-}$, $SO_3^{2-}$, $CF_3SO_2^-$, $TsO^-$, $ClO_4^-$, $F^-$, $Cl^-$, $Br^-$, $F^-$, $I^-$, $(F_3CSO_2)N^-$, $PO_4^{3-}$, wherein R is selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, alkoxy group; and wherein Z is C, N, O, or S, provided that when the backbone structural formula is

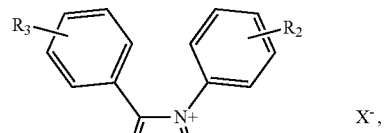

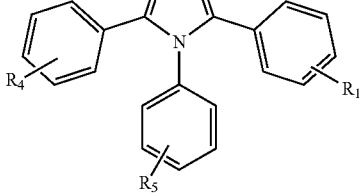

at least one of $R_2$, $R_3$, and $R_4$ is other than H.

In an embodiment, the compound is selected from:
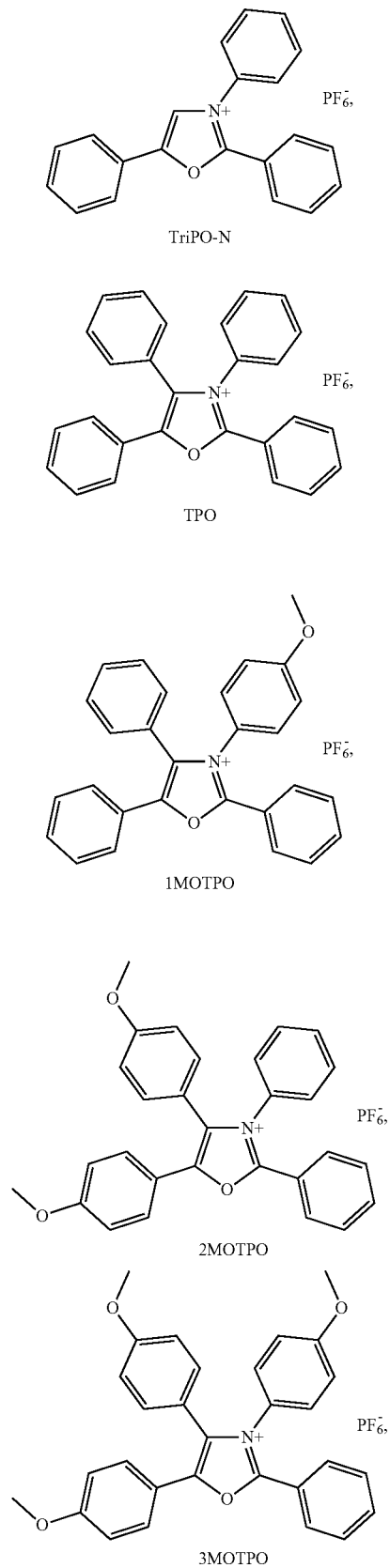
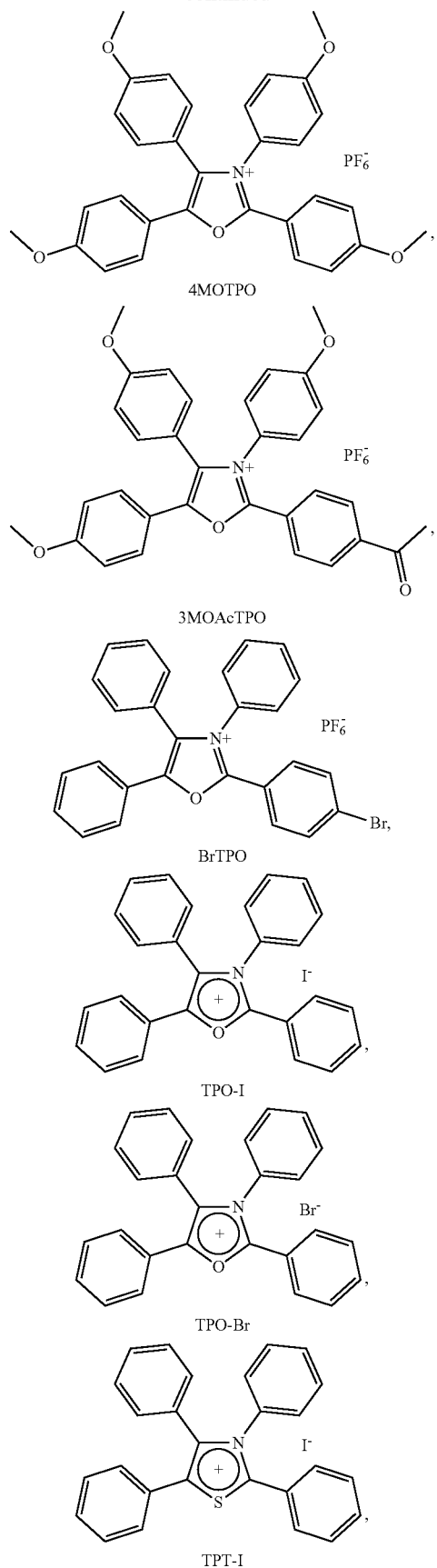

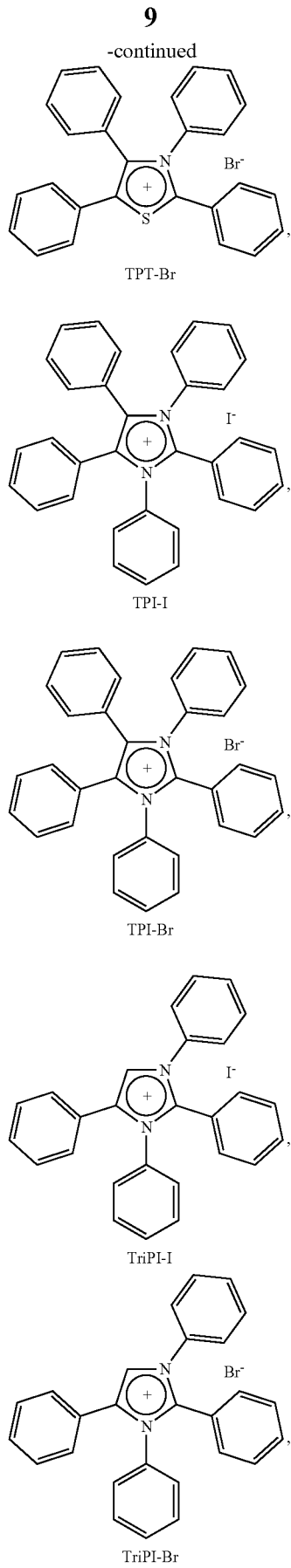

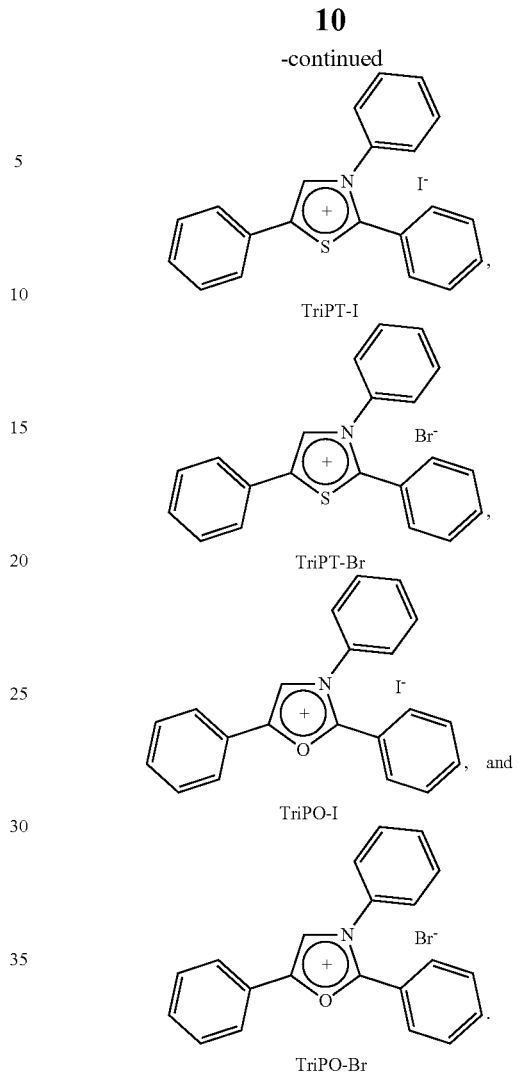

BRIEF DESCRIPTION OF DRAWINGS

Various embodiments will now be described in detail with reference to the accompanying drawings.

DETAILED DESCRIPTION

Definitions

Figure 1:
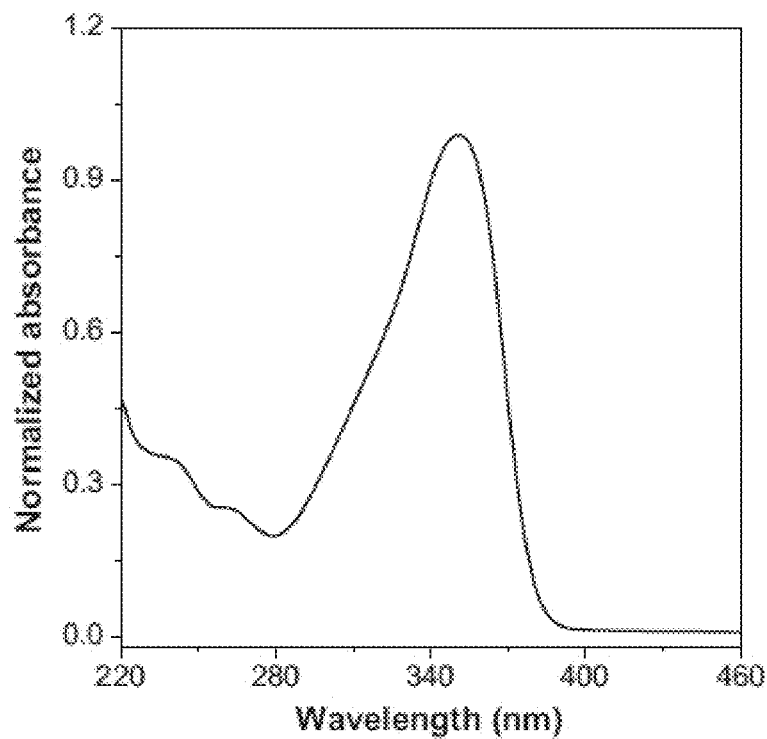
FIG. 1 depicts the absorption spectrum of TriPO-N in ethanol.

The following definitions are provided for the purpose of understanding the present subject matter and for constructing the appended patent claims.

It is noted that, as used in this specification and the appended claims, the singular forms "a", "an", and "the" include plural references unless the context clearly dictates otherwise.

The term "$\lambda_{ex}$" as used herein refers to excitation wavelength.

The phrase "aggregation caused quenching" or "ACQ" as used herein refers to the phenomenon wherein the aggregation of π-conjugated fluorophores significantly decreases the fluorescence intensity of the fluorophores. The aggregate formation is said to "quench" light emission of the fluorophores.

The phrase "aggregation induced emission" or "AIE" as used herein refers to the phenomenon manifested by compounds exhibiting significant enhancement of light-emission upon aggregation in the amorphous or crystalline (solid) states whereas they exhibit weak or almost no emission in dilute solutions.

"Emission intensity" as used herein refers to the magnitude of fluorescence/phosphorescence normally obtained from a fluorescence spectrometer or fluorescence microscopy measurement; "fluorophore" or "fluorogen" as used herein refers to a molecule which exhibits fluorescence; "luminogen" or "luminophore" as used herein refers to a molecule which exhibits luminescence; and "AIEgen" as used herein refers to a molecule exhibiting AIE characteristics.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_{1-40}$ alkyl group), for example, 1-30 carbon atoms (i.e., $C_{1-30}$ alkyl group). In some embodiments, an alkyl group can have 1 to 6 carbon atoms, and can be referred to as a "lower alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S-0 bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

As used herein, a "donor" material refers to an organic material, for example, an organic nanoparticle material, having holes as the majority current or charge carriers.

As used herein, an "acceptor" material refers to an organic material, for example, an organic nanoparticle material, having electrons as the majority current or charge carriers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Compounds

According to an embodiment, the present subject matter relates to compounds having a backbone structural formula selected from the group consisting of:

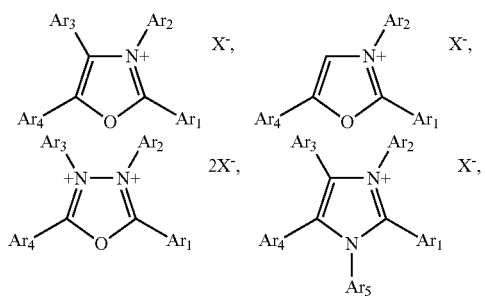

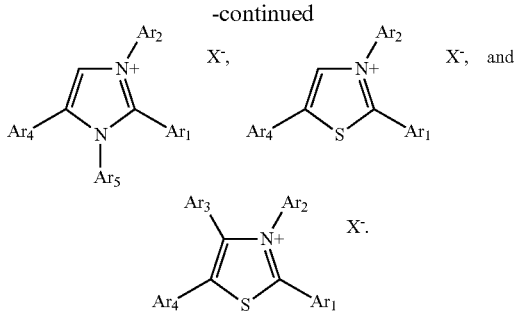

-continued wherein each of $Ar_1$, $Ar_2$, $Ar_3$, $Ar_4$, and $Ar_5$ is independently an aryl, heteroaryl, or heterocyclic group, the aryl, heteroaryl, or heterocyclic group being unsubstituted or substituted with one or more substituents selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, alkoxy group,

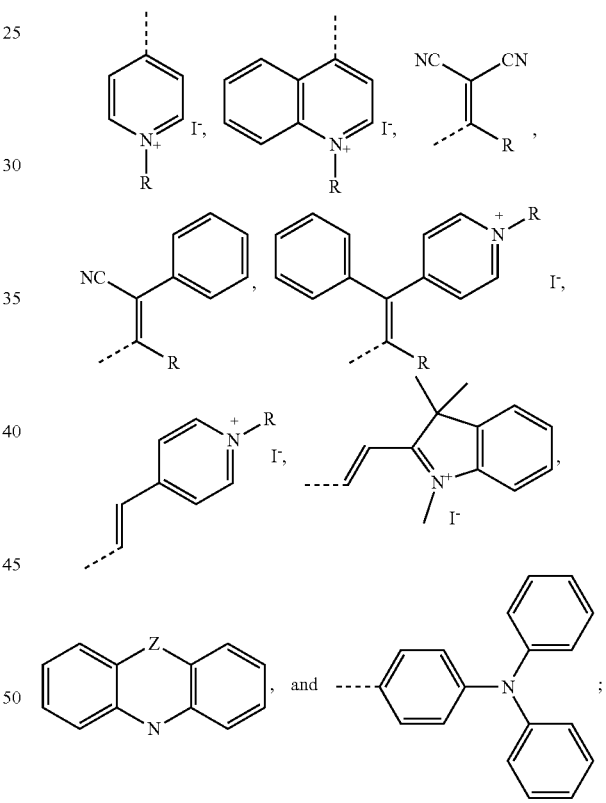

wherein $X^-$ is selected from the group consisting of $PF_6^-$, $BF_4^-$, $SbF_5^-$, $CH_3COO^-$, $CF_3COO^-$, $CO_3^{2-}$, $SO_4^{2-}$, $SO_3^{2-}$, $CF_3SO_2^-$, $TsO^-$, $ClO_4^-$, $F^-$, $Cl^-$, $Br^-$, $I^-$, $(F_3CSO_2)N^-$, and $PO_4^{3-}$;

wherein R is selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, alkoxy group; and wherein Z is C, N, O, or S.

According to some embodiments, when the backbone structural formula is

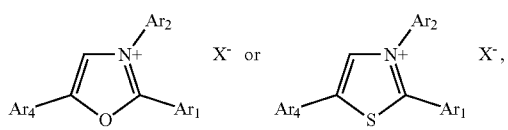

at least one of $Ar_1$, $Ar_2$, and $Ar_4$ is other than phenyl, or if $Ar_2$ and $Ar_4$ are both phenyl, An is other than phenyl, methoxyphenyl, or chlorophenyl.

According to some embodiments, when the backbone structural formula is

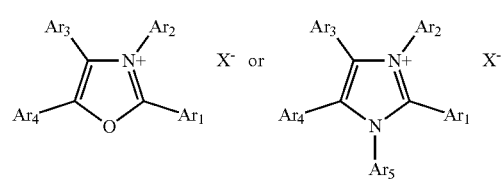

at least one of $Ar_2$, $Ar_3$, and $Ar_4$ is other than unsubstituted phenyl.

According to a further embodiment, the compounds have a backbone structural formula selected from:

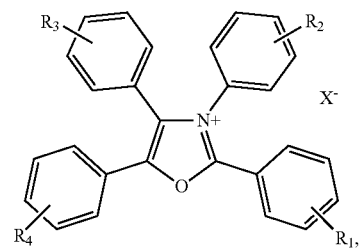

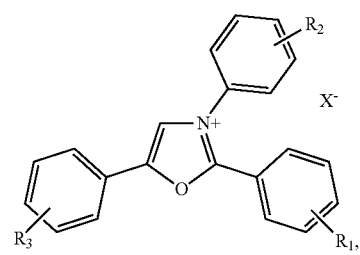

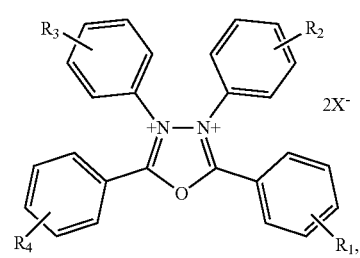

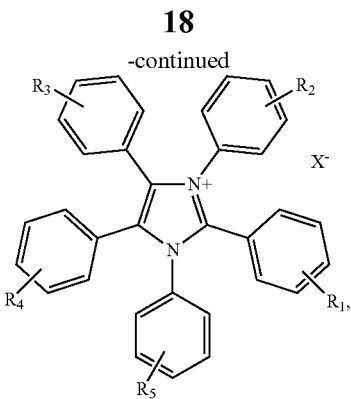

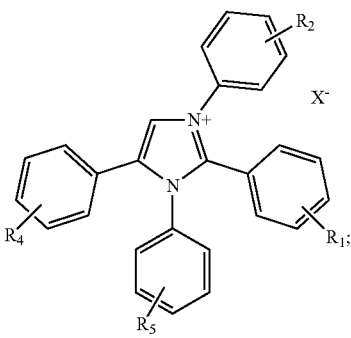

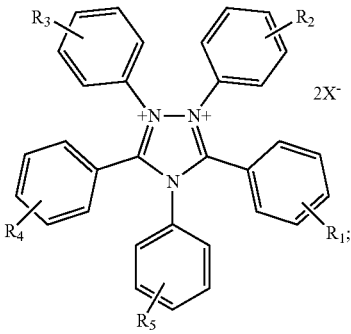

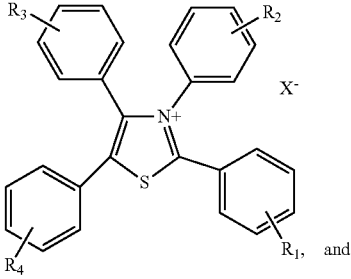

and

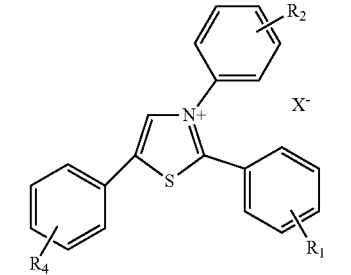

wherein each of $R_1$, $R_2$, $R_3$, $R_4$, and $R_5$ is independently selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, alkoxy group,

19

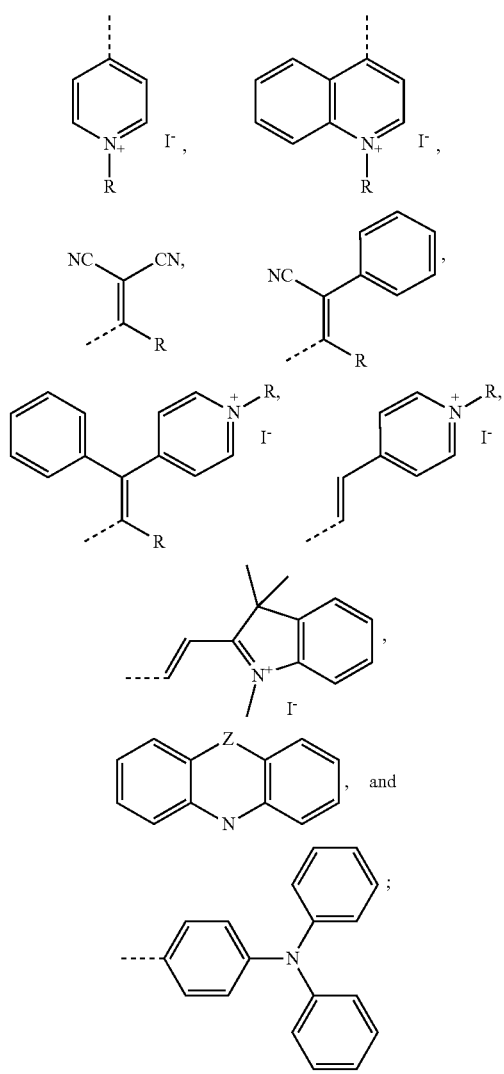

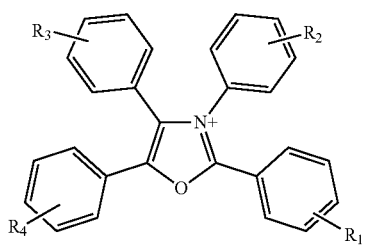

wherein X is selected from the group consisting of $PF_6^-$, $BF_4^-$, $SbF_5^-$, $CH_3COO^-$, $CF_3COO^-$, $CO_3^{2-}$, $SO_4^{2-}$, $SO_3^{2-}$, $CF_3SO^{2-}$, $TsO^-$, $ClO_4^-$, $F^-$, $Cl^-$, $Br^-$, $I^-$, $(F_3CSO_2)N^-$, $PO_4^{3-}$, wherein R is selected from the group consisting of H, F, Cl, Br, I, alkyl, unsaturated alkyl, heteroalkyl, cycloalkyl, heterocycloalkyl, aryl, heteroaryl, carboxyl group, amino group, sulfonic group, alkylthio, alkoxy group; and wherein Z is C, N, O, or S, provided that when the backbone structural formula is

20

-continued

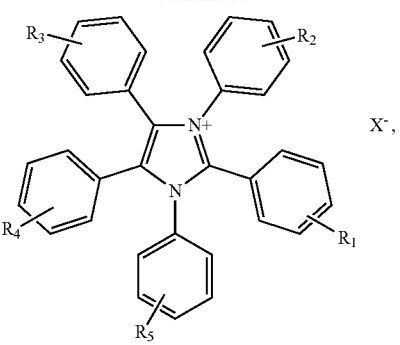

at least one of $R_2$, $R_3$, and $R_4$ is other than H.

In an embodiment, the compounds are selected from:

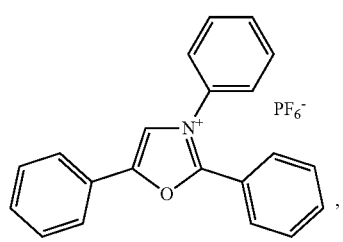

TriPO-N

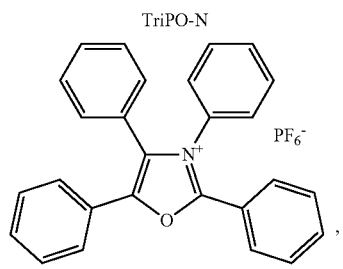

TPO

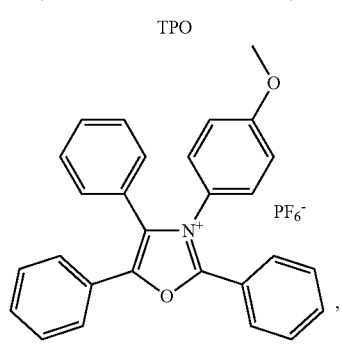

1MOTPO

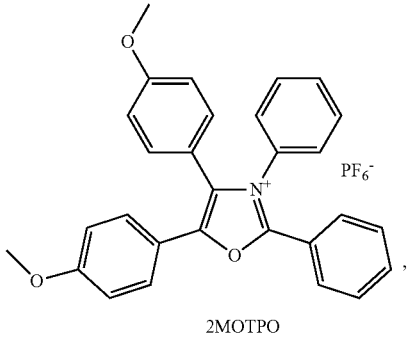

2MOTPO

-continued
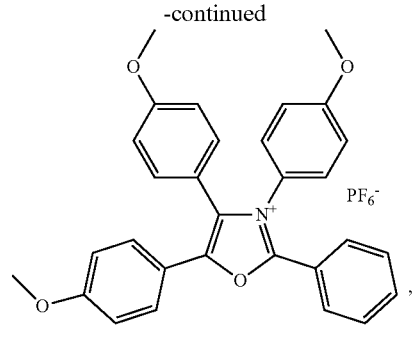
3MOTPO
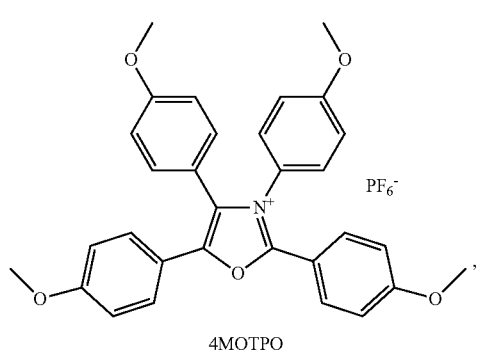
4MOTPO
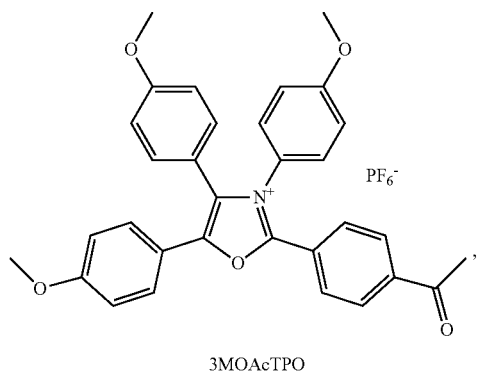
3MOAcTPO
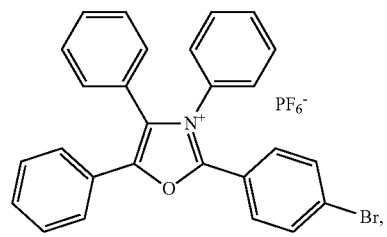
BrTPO
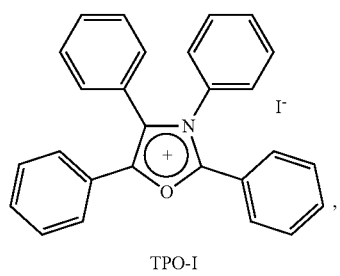
TPO-I
-continued
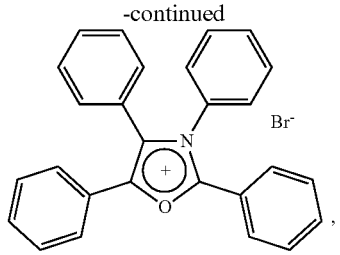
TPO-Br
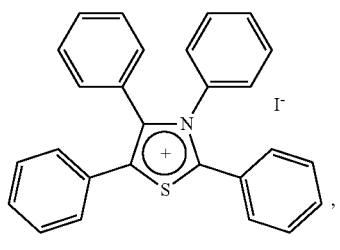
TPT-I
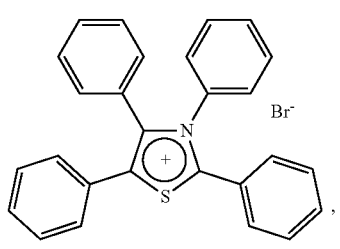
TPT-Br
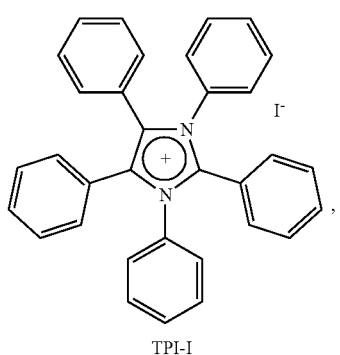
TPI-I
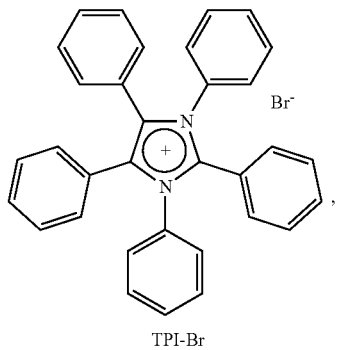
TPI-Br -continued

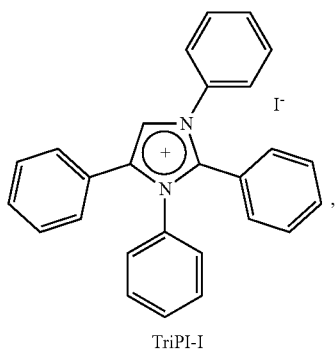
TriPI-I

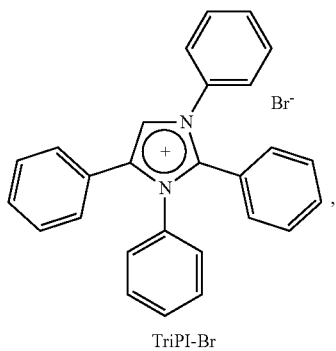
TriPI-Br

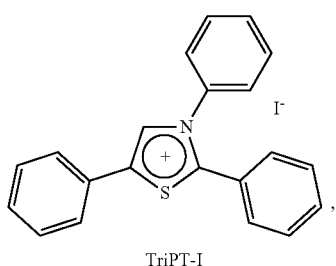
TriPT-I

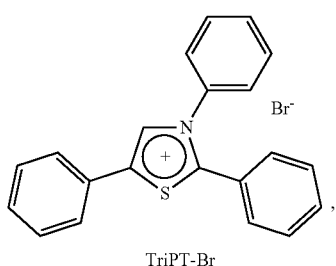
TriPT-Br

-continued

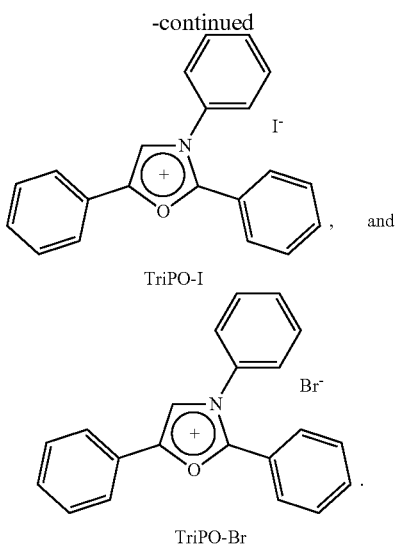
TriPO-I, and

TriPO-Br.

The counterion of the present compounds can be selected from $PF_6^-$, $BF_4^-$, $SbF_5^-$, $CH_3COO^-$, $CF_3COO^-$, $CO_3^{2-}$, $SO_4^{2-}$, $SO_3^{2-}$, $CF_3SO_2^-$, $TSO^-$, $ClO_4^-$, $F^-$, $I^-$, $Br^-$, $Cl^-$, $(F_3CSO_2)N^-$, and $PO_4^{3-}$. It should be understood that the counterions described herein in some embodiments do not include anions of trifluoromethanesulfonate or triflate ($^-OTf$).

Compound Properties

The present compounds can be functionalized based on the presence of a donor group and an acceptor group. The present compounds, for example embodiments functionalized with a donor group and an acceptor group, can be used as a probe in imaging methods. The imaging methods can include, for example, fluorescence imaging in far red and near infrared spectral regions. A target cell can be contacted with the present compounds and fluorescence imaging can be conducted on the contacted target cell.

The present compounds can be used in cellular imaging methods to detect the presence or absence of a target of interest in a target cell. The target cell can be contacted with one or more of the present compounds and the presence or absence of the target of interest can be detected using an imaging method. The target of interest can include at least one of a biomolecule, a drug, a protein, and a cellular organelle. The cellular organelle can be a mitochondrion, for example.

The present compounds can provide white light emission in thin films, such as thin polymer films. The thin polymer films can include polystyrene (PS) and/or polyethylene glycol (PEG) films, for example. The present compounds can be added to polymer films that are used to coat materials intended for 3D printing. For example, the present compounds are suitable additives for polymer films used to coat white lamp fixtures, such as lamp shades.

The present compounds can be used to stop or inhibit bacterial growth by contacting bacteria with one or more of the present compounds. The bacteria that can be inhibited or stopped from growing by contacting the present compounds can include *Staphylococcus aureus*, for example.

AIE Activity

The present subject matter contemplates organic water-soluble compounds having aggregation-induced emission (AIE) characteristics. The present compounds can include aromatic salts having an organic ion and a counterion. The aromatic salts can have anion-$\pi^+$ interactions.

The organic ion bears a positive charge and can have a propeller-shaped, non-planar structure. In the solution state, the compounds are less emissive. In the aggregate state, emission of these compounds is induced or rejuvenated. The compounds can possess fluorescence or phosphorescene properties in the solid state. According to some embodiments, the compounds can possess both fluorescence and phosporescence properties in the solid state. The compounds can be conveniently applied in biological systems, for example, as cell imaging probes to facilitate subcellular targeting. The compounds can also be useful as room temperature luminogens for electroluminescent devices and white organic light-emitting applications.

and position of the methoxyphenyl groups on the parent oxazole ring (see, e.g., FIGS. 1-29, and 31). These luminophores exhibit maximal luminescence peaks in the visible region (419-484 nm), and high brightness in the solid state. In the solution state, these molecules are less emissive because the rotation of the aromatic rotors non-radiatively dissipates the exciton energy. While in the aggregate state, the emission of these compounds is induced or rejuvenated by the restriction of intramolecular motions (RIM) and the highly twisted molecular conformation that hampers the intermolecular $\pi$-$\pi$ stacking interaction.

4MOTPO was tested in living HeLa cells as a biosensor for bioimaging. As shown in FIGS. 30A-30D, an intense fluorescence was observed in the cellular cytoplasms, demonstrating the great potential of 4MOTPO as a fluorescent probe for biological imaging.

Photophysical properties of 1MOTPO, 2MOTPO, 3MOTPO, and 4MOTPO are provided in Table 1 below.

TABLE 1

|  | $\lambda_{abs}$ | $\lambda_{em}$ | $\tau$ (ns)$^a$ | | $\phi$ (%)$^b$ | | | $k_r$ (×10$^8$ s$^{-1}$)$^d$ | | $k_{nr}$ (×10$^8$ s$^{-1}$)$^e$ | | |
|---|---|---|---|---|---|---|---|---|---|---|---|---|
|  | (nm) | (nm) | soln$^\dagger$ | solid | soln | solid | $\alpha_{AIE}{}^c$ | soln | solid | soln | solid | LogP$^g$ |
| 1MOTPO | 332 | 433 | 0.94 | 1.38 | 0.85 | 21.54 | 25.34 | 0.09 | 1.56 | 10.55 | 5.69 | 1.02 |
| 2MOTPO | 355 | 484 | 0.91 | 3.39 | 0.50 | 36.68 | 73.36 | 0.05 | 1.08 | 10.94 | 1.87 | 1.09 |
| 3MOTPO | 364 | 480 | 0.29 | 2.54 | 0.41 | 46.88 | 114.34 | 0.14 | 1.85 | 34.34 | 2.09 | 1.29 |
| 4MOTPO | 364 | 476 | 1.37 | 3.14 | 1.42 | 71.89 | 50.63 | 0.10 | 2.29 | 7.20 | 0.89 | 1.35 |

According to some embodiments, the present compounds can possess at least one of fluorescence and room temperature phosporescence properties in the solid state. Embodiments of the present compounds which include a counterion that is a heavy-atom ion, such as I$^-$ or Br$^-$, possess room temperature phosporescence properties in the solid state. According to some embodiments, compounds having a Br$^-$ counterion possess both fluorescence and room temperature phosporescence properties in the solid state. Such compounds, possessing both fluorescence and room temperature phosporescence properties in the solid state, can be tuned as organic single-molecule white light emitters (OSMWLEs).

An exemplary compound according to the present teachings is tetraphenyloxazolium (TPO) salt. The photophysical properties (absorption and photoluminescence spectra) of the compound can be easily tuned by changing the number Room Temperature Phosphorescence and Fluorescence Emission To obtain highly efficient pure organic RTP luminogens, one strategy has been to enhance intersystem crossing by covalent bonds connecting heavy halogen atoms or carbonyl groups to the luminophor, while suppressing the non-radiative dissipation by aggregation, crystallization, or polymer matrix assisting. Numerous theories and experimental results have confirmed that the heavy-atom effect is a very effective method to enhance intersystem crossing by promoting SOC and minimizing $\Delta E_{S-T}$ between $S_1$ and $T_n$.

Figures 33A, 33B:
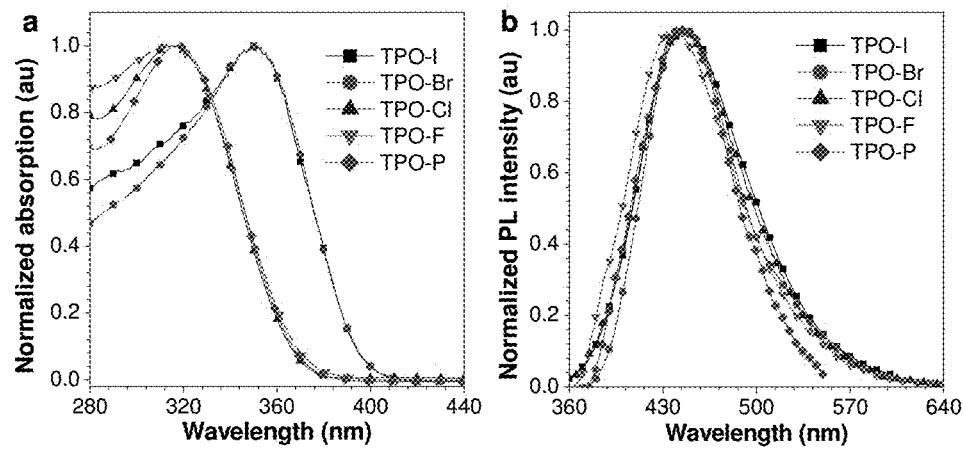
FIG. 33 depicts (a) UV-vis and (b) Photoluminescence (PL) spectra of TPO-I, TPO-Br, TPO-Cl, TPO-F and TPO-P (10 μM) in EtOH solution.
Figures 34A, 34B, 34C, 34D:
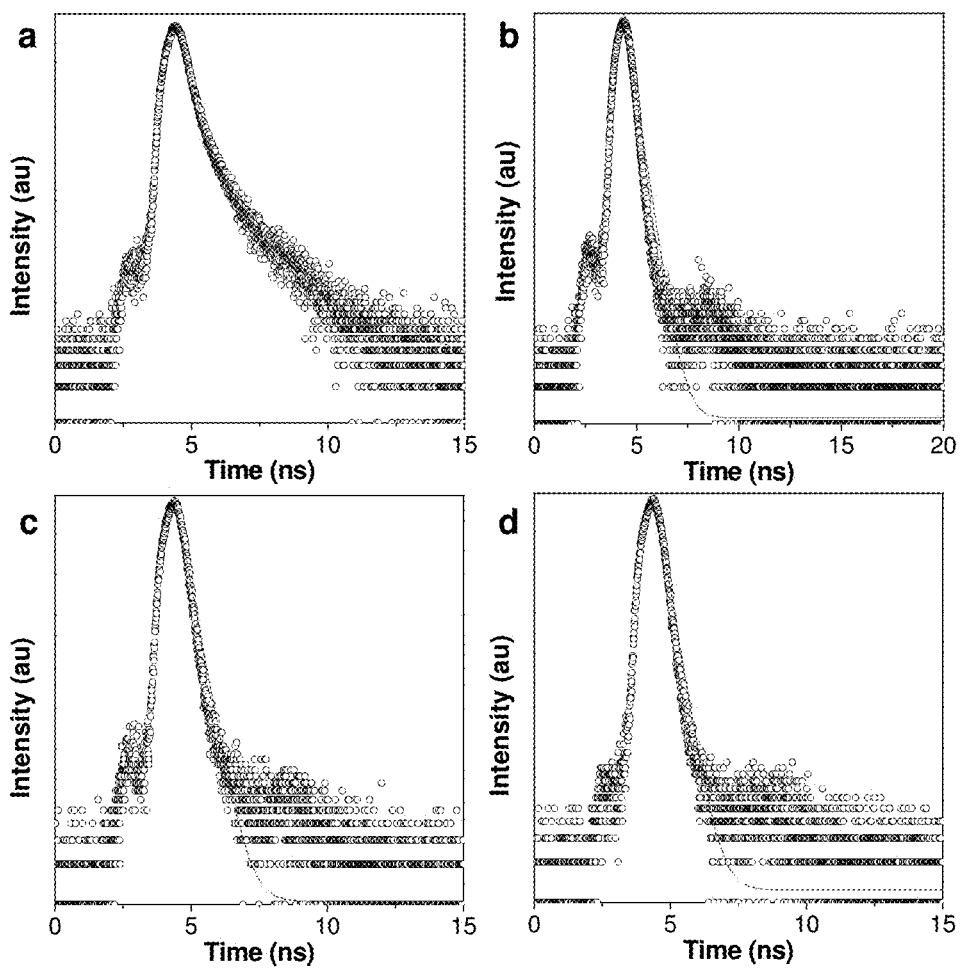
FIG. 34 depicts time-resolved PL decay of (a) TPO-I, (b) TPO-Br, (c) TPO-Cl, and (d) TPO-F at maximum emission wavelength in ethanol solution.
Figures 35A, 35B:
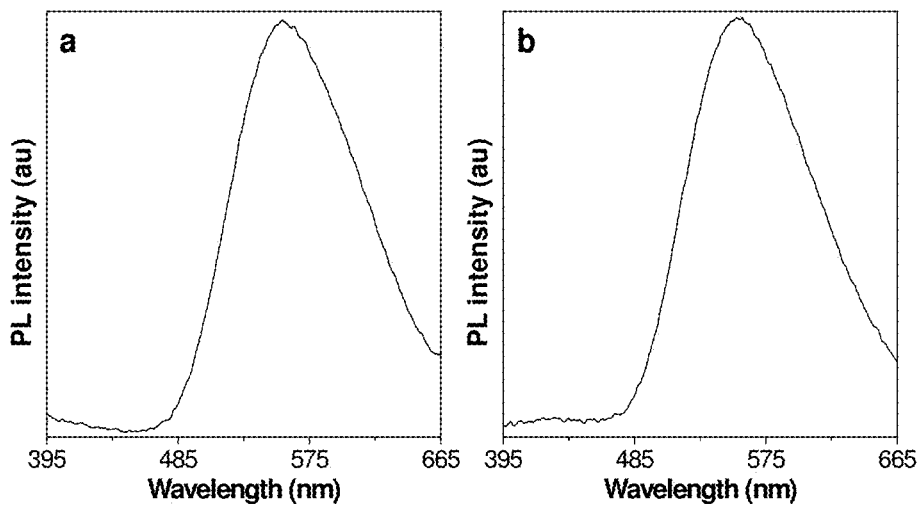
FIG. 35 depicts delayed (50 μs) PL spectra of powder of (a) TPO-I and (b) TPO-Br.
Figures 36A, 36B:
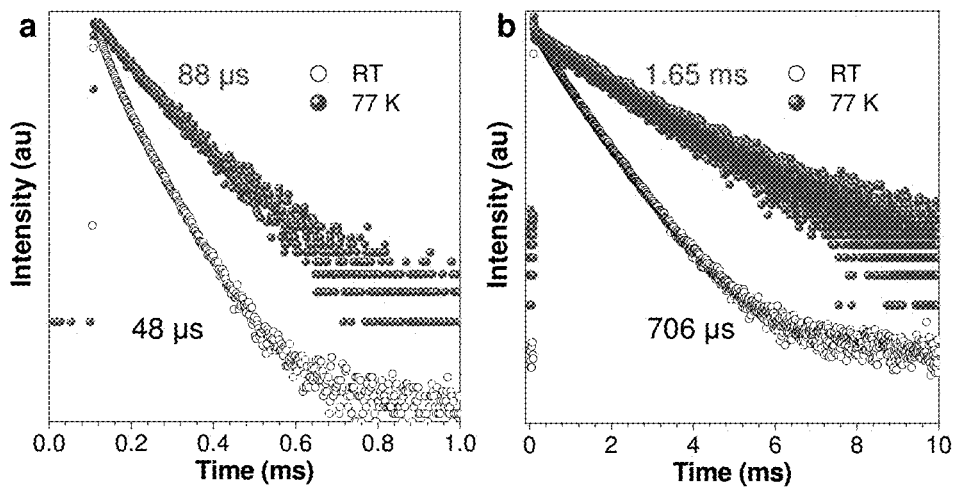
FIG. 36 depicts time-resolved PL decay of powder of (a) TPO-I at 559 nm and (b) TPO-Br at 549 nm under different temperature.
Figure 37:
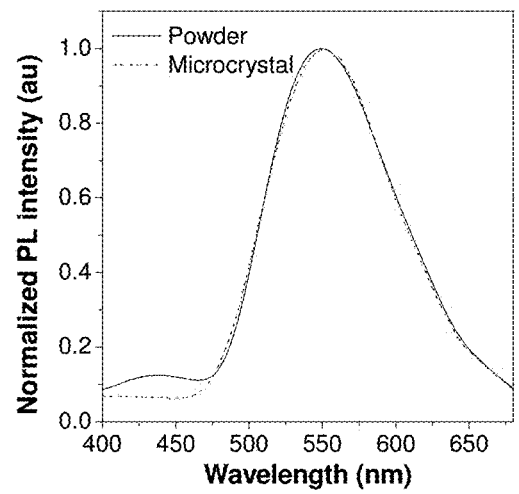
FIG. 37 depicts the PL spectra of powder and microcrystal of TPO-Br.
Figures 38A, 38B, 38C, 38D, 38E, 38F:
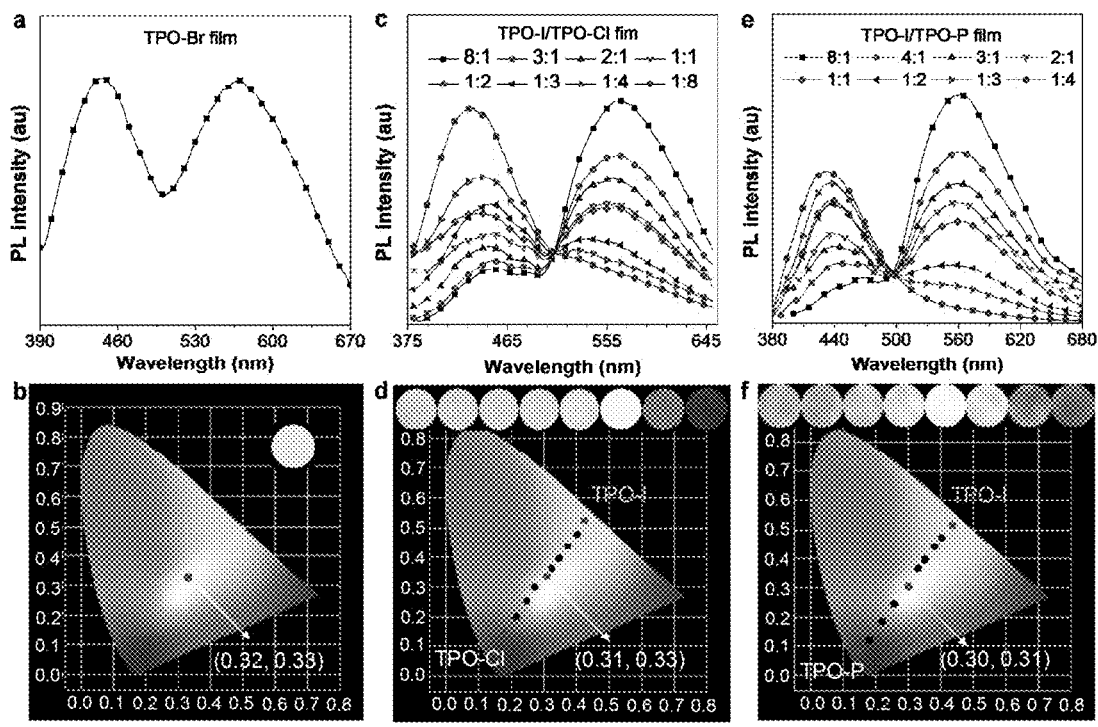
FIG. 38 depicts PL spectra of films: (a) TPO-Br only, (c) TPO-I/TPO-Cl, and (e) TPO-I/TPO-P with different molar ratios; CIE 1931 coordinates of prompt emission of films: (b) TPO-Br only, (d) TPO-I/TPO-Cl, and (f) TPO-I/TPO-P with different molar ratios (insets show fluorescent photographs of these thin films taken under 365 nm UV irradiation).
Figure 39:
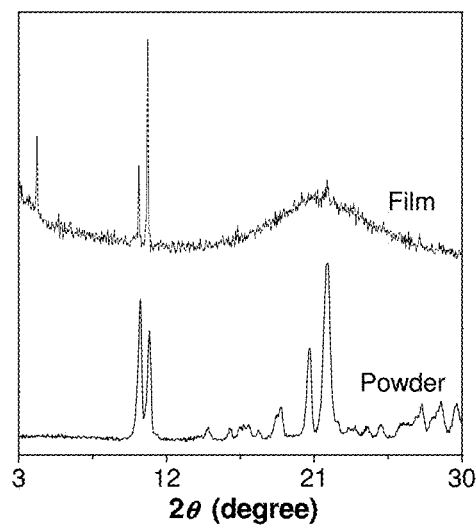
FIG. 39 depicts XRD patterns of film and powder of TPO-Br.
Figure 40:
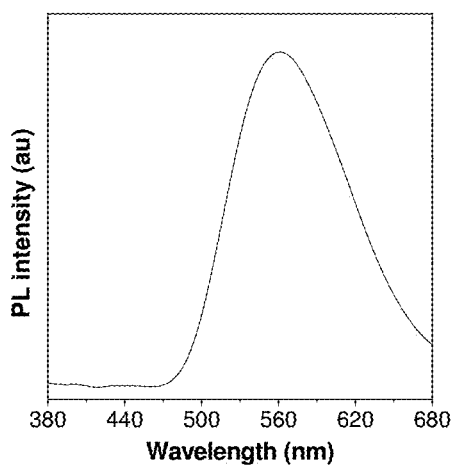
FIG. 40 depicts PL spectra of TPO-I film.
Figures 41A, 41B, 41C, 41D, 41E, 41F, 41G, 41H:
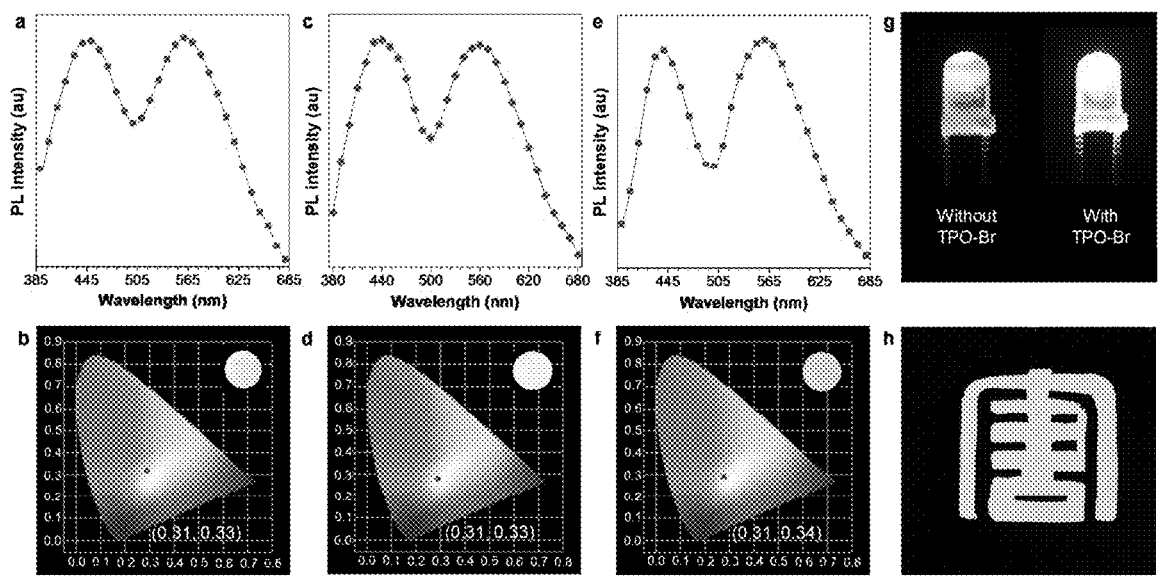
FIG. 41 depicts PL spectra and CIE 1931 coordinates of prompt emission of films in polystyrene (PS), ((a) and (b), respectively) TPO-Br, ((c) and (d), respectively) TPO-I/TPO-Cl (molar ratio=1:2), and ((e) and (f), respectively) TPO-I/TPO-P (molar ratio=1:3) in polystyrene (PS) (2%, m/m) (insets show fluorescent photographs of these films in PS taken under 365 nm UV irradiation); (g) fluorescent photographs of UV-LED lamps (Emission wavelength: 360-370 nm) coated with PS films without (left) and with (right) TPO-Br; and (h) fluorescent pattern of a Chinese character "Tang" based on the PS film (3 cm×3 cm) containing TPO-Br (2%, m/m) taken under 365 nm UV irradiation.
Figures 42A, 42B, 42C, 42D, 42E:
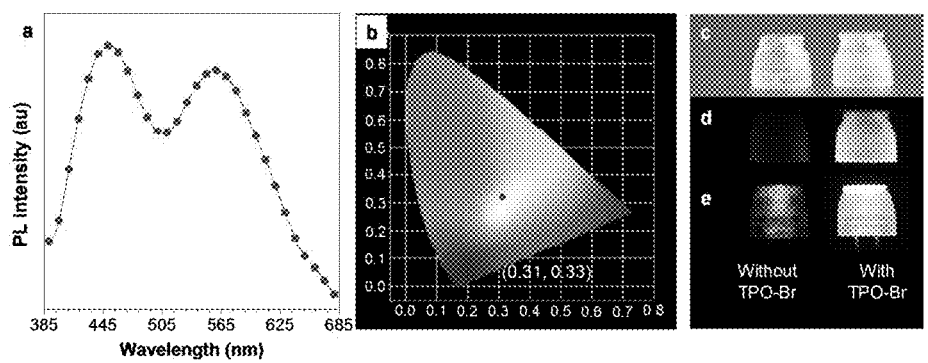
FIG. 42 depicts 3D printing white light application: (a) PL spectra, and (b) CIE 1931 coordinates of prompt emission of the PEG film containing TPO-Br (2%, m/m); (c)-(e) photographs of lampshades which were prepared by 3D printer without (left) and with (right) TPO-Br taken under (c) daylight, (d) 365 nm UV light irradiation, and (e) UV-LED lamps (lamp size of lampshades is 8.2×8.2×9.2 mm).

The present inventors have further found that anion-$\pi^+$ interactions are an efficient strategy to build strong emissive luminogens in the solid state. In the present compounds, for example, the special position of anions close to the aromatic $\pi$ systems form strong anion-$\pi^+$ interactions to block detrimental intermolecular $\pi$-$\pi$ stacking (FIGS. 32-34). The anion-$\pi^+$ interactions for TPO-I, TPO-Br, TPO-Cl, TPO-F, and TPO-P are summarized in Table 2 below.

TABLE 2

| | | $\lambda_{em}$ (nm) | | $\tau$ (ns)$^a$ | | $\phi$ (%)$^b$ | | | |
|---|---|---|---|---|---|---|---|---|---|
| AIEgens | $\lambda_{abs}$ (nm) | Soln | Solid | Soln | Solid | Soln | Solid | $\alpha_{AIE}{}^c$ | E (kcal/mol)$^d$ |
| TPO-I | 350 | 447 | 559 | 0.83 | 48740 | 0.77 | 16.00 (35.00 $^g$) | 20.78 | −71.43, −70.19 |
| TPO-Br | 352 | 442 | 434 549 | 0.40 | 2.52$^e$ 706420$^f$ | 1.08 | 17.85 (36.56 $^g$) | 16.53 | −85.17, −84.37 |
| TPO-Cl | 316 | 428 | 435 | 0.39 | 1.60 | 1.20 | 20.05 | 16.71 | / |
| TPO-F | 314 | 421 | 420 | 0.36 | 0.80 | 0.65 | 11.11 | 17.09 | / |

TABLE 2-continued

| AIEgens | $\lambda_{abs}$ (nm) | $\lambda_{em}$ (nm) Soln | $\lambda_{em}$ (nm) Solid | $\tau$ (ns)[a] Soln | $\tau$ (ns)[a] Solid | $\phi$ (%)[b] Soln | $\phi$ (%)[b] Solid | $\alpha_{AIE}$[c] | E (kcal/mol)[d] |
|---|---|---|---|---|---|---|---|---|---|
| TPO-P | 318 | 419 | 422 | 0.86 | 1.02 | 1.18 | 18.58 | 15.75 | −63.95, −71.97 |

The present inventors further found that when the counterion of the present compounds is a heavy halogen ion, at least some of the fluorescence emission can be transformed to phosphorescence emission by taking advantage of heavy-atom effects (FIGS. 35-40). For example, when the counterion of 1,2,3,4-tetraphenyloxazolium (TPO) is a heavy halogen ion, such as iodide (TPO-I) or bromide (TPO-Br), the emission of TPO-I or TPO-Br can display RTP characteristic with a long lifetime in the solid state because heavy halogen ions can trigger efficient intersystem crossing to boost the phosphorescence efficiency.

Single crystals and theoretical calculations were utilized to explore the nature of this phenomena. Single crystal structures of TPO-I and TPO-Br, respectively, showing torsion angles and anion-$\pi^+$ interactions with distances are shown below.

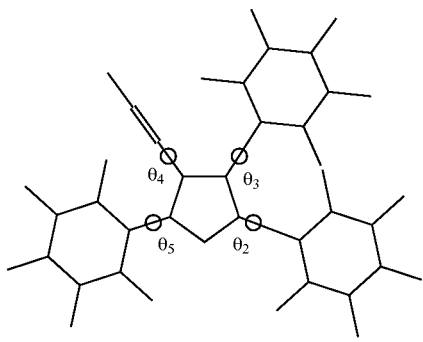

a $\theta_2 = 26.58°$  $\theta_3 = 59.98°$
$\theta_4 = 81.88°$  $\theta_5 = 15.85°$

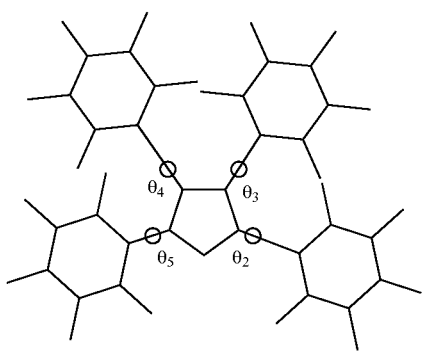

b $\theta_2 = 41.97°$  $\theta_3 = 64.99°$
$\theta_4 = 51.86°$  $\theta_5 = 37.76°$ -continued

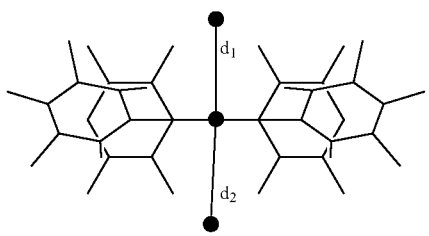

c $d_1 = 3.980$ Å, $d_2 = 4.071$ Å

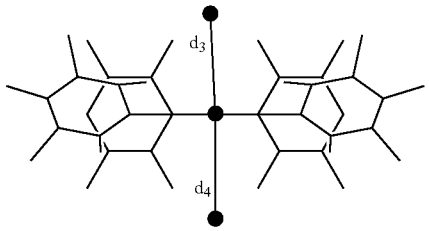

d $d_3 = 3.494$ Å, $d_2 = 3.601$ Å

The present inventors also found that TPO-Br demonstrates dual emission, i.e., both fluorescence and phosphorescence, in the solid state. It was found that under certain conditions, the dual emission of TPO-Br can be tuned to obtain OSMWLEs. However, in the absence of heavy counterions, e.g., in the case of TPO-P, TPO-Cl, and TPO-F, only fluorescence emission was observed. This verifies the crucial role of heavy-atom-participated anion-$\pi^+$ interactions.

The present compounds can provide white light emission in thin films, e.g., polymer films. The present compounds are suitable additives for polymer films (FIGS. 41A-41F and FIGS. 42A-42B), used in materials intended for 3D printing. For example, the present compounds can be added to 3D printing material used to prepare white-light fixtures, e.g., lampshades. FIGS. 41G-41H and FIGS. 42C-42E demonstrate the effective incorporation of TPO-Br in lampshades prepared by a 3D printer. The present teachings demonstrate the significance of heavy-atom-participated anion-$\pi^+$ interactions in RTP luminogens for OSMWLEs application and 3D printing white-light objects.

As described herein, anion-$\pi^+$ interactions can enhance the heavy-atom effect of heavy halogen ions to provide highly efficient RTP materials. As set forth in detail below, five 1,2,3,4-tetraphenyloxazolium (TPO) derivatives with different counterions (such as: I$^-$, Br$^-$, Cl$^-$, F$^-$, or PF$_6^-$) were synthesized and their single crystal structures confirmed the existence of anion-$\pi^+$ interactions. Photophysical properties confirmed that TPO-I, with strong anion-$\pi^+$ interactions and heavy-atom effect, has full RTP features. TPO-Br, with relatively weak heavy-atom effect, has both fluorescence and RTP characteristic. Theoretical calculation results verified that heavy halogen ions can effectively decrease the energy gap ($\Delta E_{SlTn}$) and increase the spin-orbit coupling constant ($\xi_{SlTn}$) of luminogens with anion-$\pi^+$ interactions to facilitate the occurrence of intersystem crossing (ISC) process. Moreover, the dual emissions of TPO-Br can be tuned by controlling the proportion present in the amorphous and crystalline states to achieve properties of an organic single-molecule white light emitter (OSMWLE). For example, TPO derivatives with anion-$\pi^+$ interactions can be configured to emit white light by tuning the content of the different counterions.

The present teachings are illustrated by the following examples.

EXAMPLES

Materials and Instruments $^1$H and $^{13}$C NMR spectra were measured on a Bruker ARX 400 NMR spectrometer using chloroform, MeOD or DMSO as solvent and tetramethylsilane (TMS, $\delta=0$) as internal reference. High-resolution mass spectra (HRMS) were recorded on a Finnigan MAT TSQ 7000 Mass Spectrometer System operated in a MALDI-TOF mode. Absorption spectra were recorded on a Shimadzu UV-3600 spectrophotometer. Photoluminescence (PL) spectra were recorded on Fluorolog®-3 spectrofluorometer. Single-crystal X-ray diffraction measurements were conducted on a Bruker-Nonius Smart Apex CCD diffractometer with graphite monochromated Mo K$\alpha$ radiation. The photoluminescence quantum yields were measured using a Hamamatsu absolute PL quantum yield spectrometer C11347 Quantaurus-QY. Transient PL at room temperature was measured using Quantaurus-Tau fluorescence lifetime measurement system (C11367-03, Hamamatsu Photonics Co., Japan). Laser confocal scanning microscope images were collected on Zeiss laser scanning confocal microscope (LSM7 DUO) and analyzed using ZEN 2009 software (Carl Zeiss). Powder and film X-ray diffraction was performed using a Philips PW 1830 X-ray Diffractometer.

For cell culturing, HeLa cells were cultured in MEM containing 10% FBS and antibiotics (100 units/mL penicillin and 100 g/mL streptomycin) in a 5% $CO_2$ humidity incubator at 37° C. All culture mediums supplemented with 10% heat-inactivated FBS, 100 units/mL penicillin and 100 pg/mL streptomycin. Before experiment, the cells were precultured until confluence was reached.

For cell imaging, HeLa cells were grown overnight on a 35 mm petri dish with a cover slip at 37° C. After the removal of the medium, the adherent cells were washed twice with 1× phosphate buffered saline (PBS) buffer. 4MOTPO were then added to the chamber. After incubation for 1 h, then washed and incubated with MitoTracker® Green FM and NucRed® Live for 10 min, followed by further washing three times with 1×PBS buffer. The cells were imaged on Zeiss laser scanning confocal microscope and analyzed using ZEN 2009 software.

Example 1

Synthesis and Characterization of TriPO-N

An exemplary reaction scheme for preparing TriPO-N is as provided below:

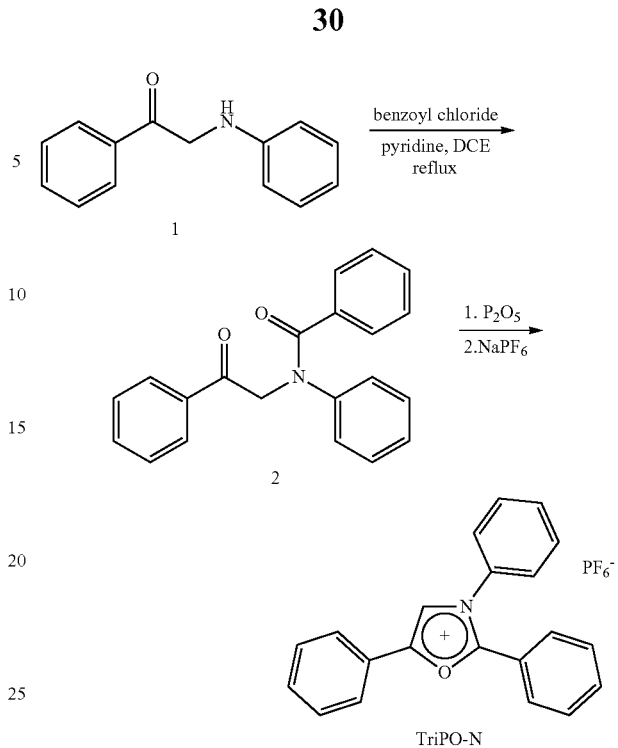

Synthesis of Compound 2

Benzoyl chloride (0.82 mL, 7.00 mmol) was added to a solution of 1 (1.00 g, 4.73 mmol) and pyridine (1.11 mL, 14.10 mmol) in 1, 2-dichloroethane (30 mL) and refluxed under nitrogen for 12 h. The reaction mixture was cooled to room temperature and washed with $Na_2CO_3$ solution (3×30 mL). The organic layer was dried over sodium sulfate. After evaporation of the solvent under vacuum, the residue was subjected to flash column chromatography with hexane/EA (20:1, v/v) to give white solid 2 (1.10 g, 74%). $^1$H NMR (400 MHz, $CDCl_3$) δ 8.01 (d, J=7.3 Hz, 2H), 7.59 (t, J=7.4 Hz, 1H), 7.48 (t, J=7.6 Hz, 2H), 7.41 (d, J=7.0 Hz, 2H), 7.28-7.09 (m, 8H), 5.35 (s, 2H). $^{13}$C NMR (101 MHz, $CDCl_3$) δ 192.86, 170.12, 143.42, 134.67, 134.52, 133.03, 129.21, 128.47, 128.27, 128.16, 127.41, 127.12, 126.93, 126.19, 56.50.

Synthesis of TriPO-N

Compound 2 (0.50 g, 1.59 mmol) and phosphorus pentoxide (0.27 g, 1.91 mmol) were dissolved in dry DCM (1.0 mL) and heated under nitrogen at 180° C. for 4 h. The reaction mixture was cooled to −20° C. The solution of $NaPF_6$ (1.33 g, 7.95 mmol) in $H_2O$ and acetone (10 mL) was added to the reaction mixture and stirred at −20° C. for 30 min. The mixture was slowly warmed to room temperature and stirred for 2 h. Acetone was removed under vacuum. The solid was filtered, washed with water and purified by flash column chromatography (DCM:Methanol=1:0-10:1) to afford the desired compound TriPO-N (215 mg, 31%). $^1$H NMR (400 MHz, MeOD) δ 8.74 (s, 1H), 8.01 (d, J=5.5 Hz, 2H), 7.75 (m, 8H), 7.65 (m, 3H), 7.58 (t, J=7.9 Hz, 2H). $^{13}$C NMR (101 MHz, MeOD) δ 159.20, 152.63, 134.12, 133.14, 131.30, 130.74, 130.02, 128.94, 128.70, 128.65, 124.79, 124.45, 123.35, 119.37, 118.64. HRMS (MALDI-TOF) m/z: $[M-PF6]^+$ calcd for $C_{21}H_{16}NO^+$, 298.1226, found, 298.1212.

Figure 2:
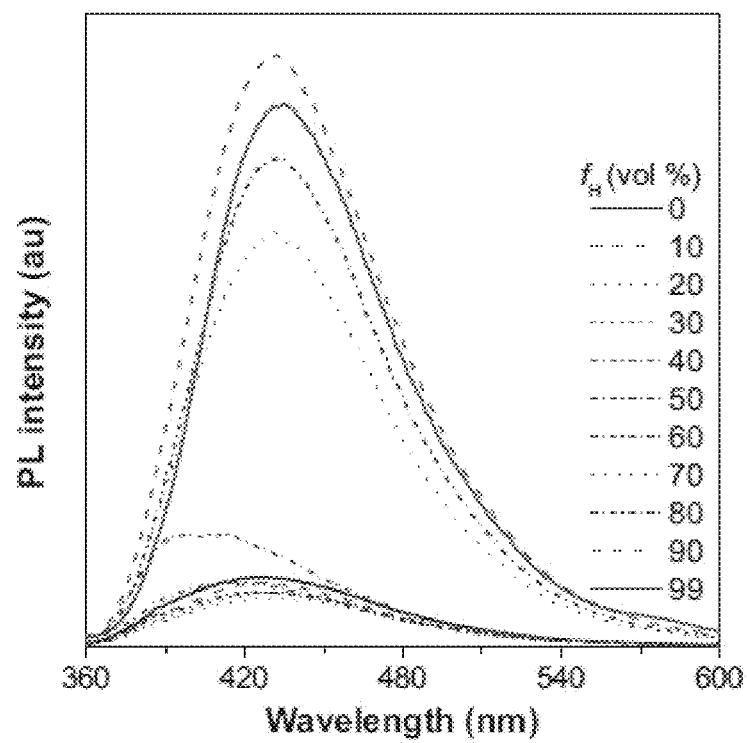
FIG. 2 depicts the PL spectra of TriPO-N in THF/hexane mixtures with different hexane fractions ($f_H$) (excitation at 350 nm).

FIG. 1 depicts the absorption spectrum of TriPO-N in ethanol. FIG. 2 depicts the PL spectra of TriPO-N in THF/hexane mixtures with different hexane fractions (fH)

Figure 3:
FIG. 3 depicts fluorescent photographs of TriPO-N in THF/hexane mixtures with different $f_H$ taken under 365 nm UV irradiation (concentration: 10 μM).
Figure 4:
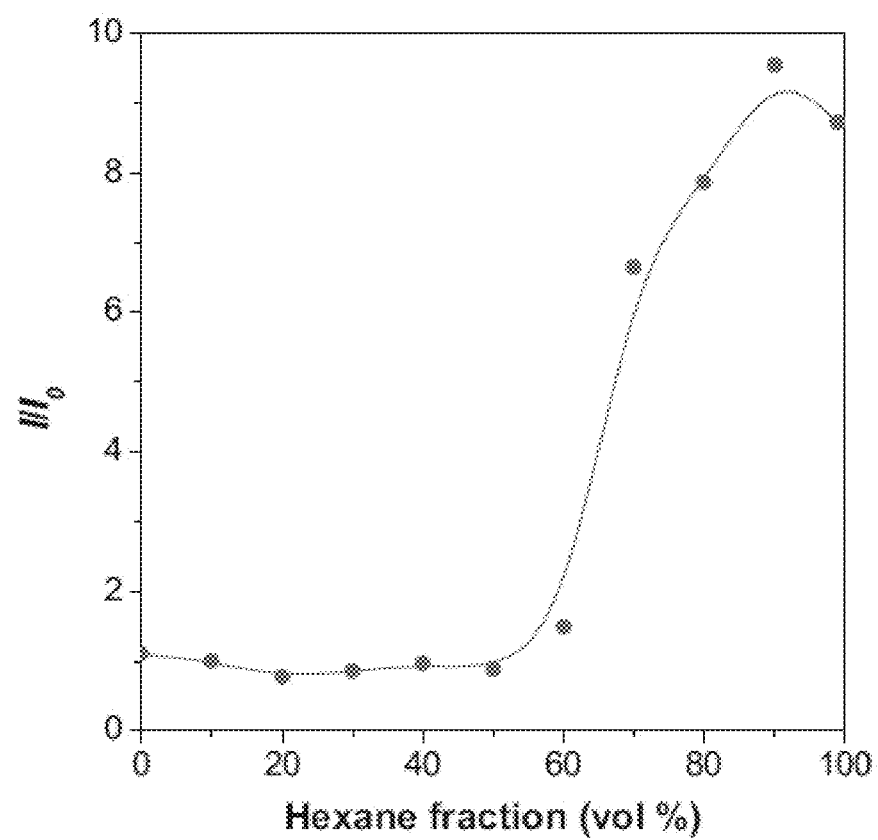
FIG. 4 depicts a plot of relative PL intensity ($I/I_0$) versus the composition of the THF/hexane mixtures of TriPO-N. $I_0$=PL intensity in pure THF.

(excitation at 350 nm). FIG. 3 depicts fluorescent photographs of TriPO-N in THF/hexane mixtures with different fH taken under 365 nm UV irradiation (concentration: 10 μM). FIG. 4 depicts a plot of relative PL intensity (I/I0) versus the composition of the THF/hexane mixtures of TriPO-N. I0=PL intensity in pure THF.

Example 2

Synthesis and Characterization of TPO

An exemplary reaction scheme for preparing TPO is as provided below:

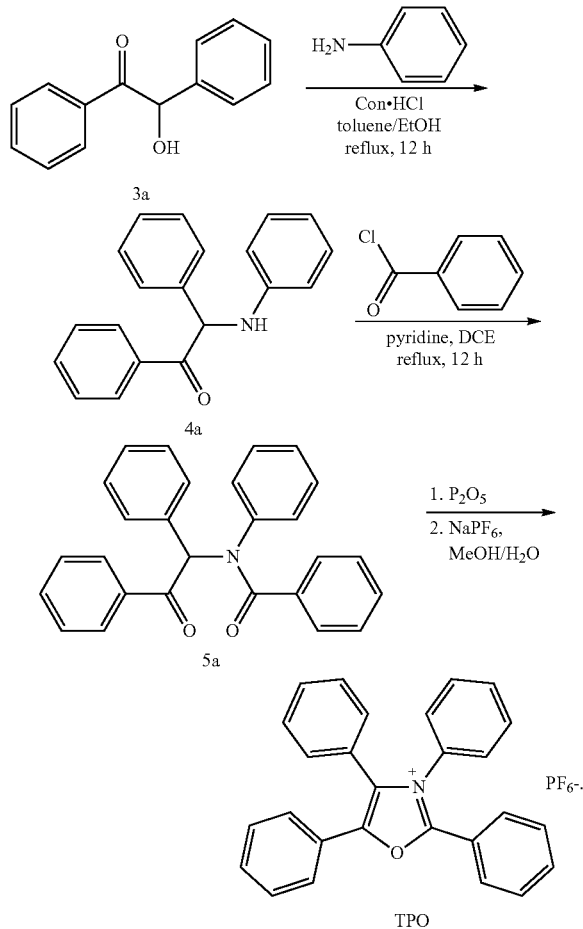

Synthesis of Compound 4a

To a solution of 3a (2.12 g, 10.00 mmol) and aniline (1.12 g, 12.00 mmol) in toluene:EtOH=10:1 (40 mL) were added ten drops of concentrated HCl. The reaction mixture was stirred and refluxed for 12 h. After cooling the reaction mixture to room temperature, the precipitate was filtered under vacuum. The solid was added to ethyl acetate and $K_2CO_3$ solution. The aqueous phase was extracted with ethyl acetate. The combined organic layers were washed with brine, dried over anhydrous sodium sulfate and concentrated under reduced pressure. The residue was purified by flash column chromatography with Hexane/EA (10:1-2:1, v/v) to afford the desired compound 4a as light white solid (2.41 g, 84%). $^1$H NMR (400 MHz, MeOD) δ 8.05 (d, J=7.5 Hz, 2H), 7.53 (t, J=7.1 Hz, 1H), 7.49-7.37 (m, 4H), 7.24 (t, J=7.2 Hz, 2H), 7.16 (t, J=7.1 Hz, 1H), 7.05 (t, J=7.4 Hz, 2H), 6.73 (d, J=7.6 Hz, 2H), 6.60 (t, J=7.0 Hz, 1H), 6.21 (s, 1H). $^{13}$C NMR (101 MHz, MeOD) δ 197.23, 145.99, 137.25, 134.62, 132.54, 127.95, 127.92, 127.83, 127.73, 127.49, 126.97, 116.72, 113.02, 61.73. HRMS (MALDI-TOF) m/z: [M+H]$^+$ calcd for $C_2OH_{18}NO$, 288.1388, found, 288.1393.

Synthesis of Compound 5a

Benzoyl chloride (0.82 mL, 7.00 mmol) was added to a solution of 4a (1.36 g, 4.73 mmol) and pyridine (1.11 mL, 14.10 mmol) in 1, 2-dichloroethane (30 mL) and refluxed under nitrogen for 12 h. The reaction mixture was cooled to room temperature and washed with $Na_2CO_3$ solution (3×30 mL). The organic layer was dried over sodium sulfate. After evaporation of the solvent under vacuum, the residue was subjected to flash column chromatography with hexane/EA (20:1, v/v) to give white solid 5a (1.52 g, 82%). $^1$H NMR (400 MHz, CD$_2$Cl$_2$) δ 8.02 (d, J=7.5 Hz, 2H), 7.53 (d, J=7.0 Hz, 1H), 7.44 (t, J=7.2 Hz, 2H), 7.30 (d, J=7.6 Hz, 2H), 7.24 (s, 1H), 7.23-7.12 (m, 7H), 6.99 (s, 4H). $^{13}$C NMR (101 MHz, CD$_2$Cl$_2$) δ 195.26, 170.03, 139.79, 135.63, 135.18, 132.84, 132.40, 130.69, 130.38, 128.64, 127.98, 127.95, 127.93, 127.81, 127.71, 127.34, 126.91, 126.33, 66.81. HRMS (MALDI-TOF) m/z: [M+H]$^+$ calcd for $C_{27}H_{22}NO_2$, 392.1651, found, 392.1671.

Synthesis of TPO

Compound 5a (0.50 g, 1.28 mmol) and phosphorus pentoxide (0.22 g, 1.54 mmol) were dissolved in dry DCM (1.0 mL) and heated under nitrogen at 180° C. for 4 h. The reaction mixture was cooled to −20° C. The solution of NaPF$_6$ (1.07 g, 6.40 mmol) in H$_2$O and acetone (10 mL) was added to the reaction mixture and stirred at −20° C. for 30 min. The mixture was slowly warmed to room temperature and stirred for 2 h. Acetone was removed under vacuum. The solid was filtered, washed with water and purified by flash column chromatography (DCM:Methanol=1:0-10:1) to afford the desired compound TPO (345 mg, 52%) as white solid. $^1$H NMR (400 MHz, DMSO) δ 7.78-7.70 (m, 3H), 7.69-7.63 (dd, J=13.0, 5.5 Hz, 4H), 7.61-7.46 (m, 13H). $^{13}$C NMR (101 MHz, DMSO) δ 158.59, 146.93, 134.72, 131.71, 131.40, 131.23, 131.02, 130.83, 130.41, 130.23, 129.50, 129.41, 129.33, 127.26, 125.55, 124.18, 122.70, 120.10. HRMS (MALDI-TOF) m/z: [M-PF6]$^+$ calcd for $C_{27}H_{20}NO^+$, 374.1539, found, 374.1544.

Figure 5:
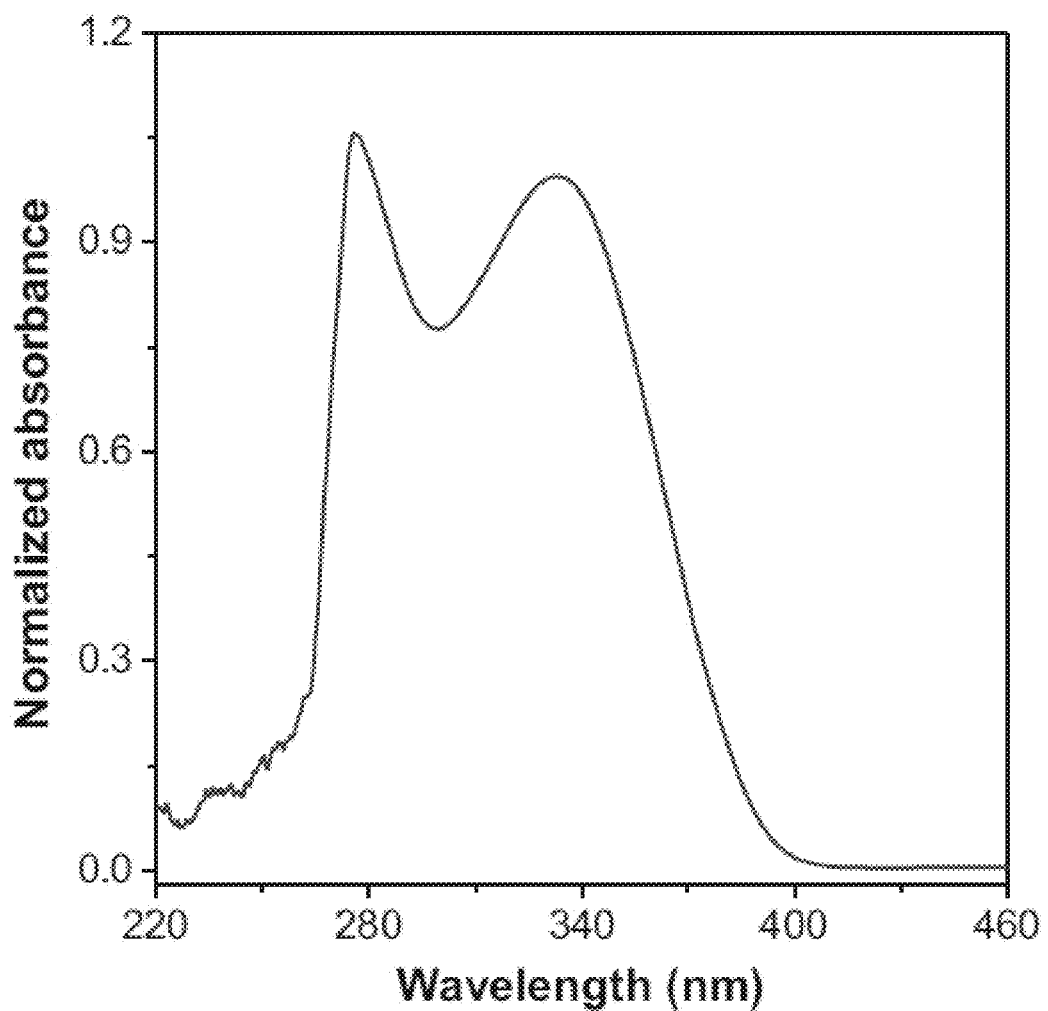
FIG. 5 depicts the absorption spectrum of TPO in ethanol.
Figure 6:
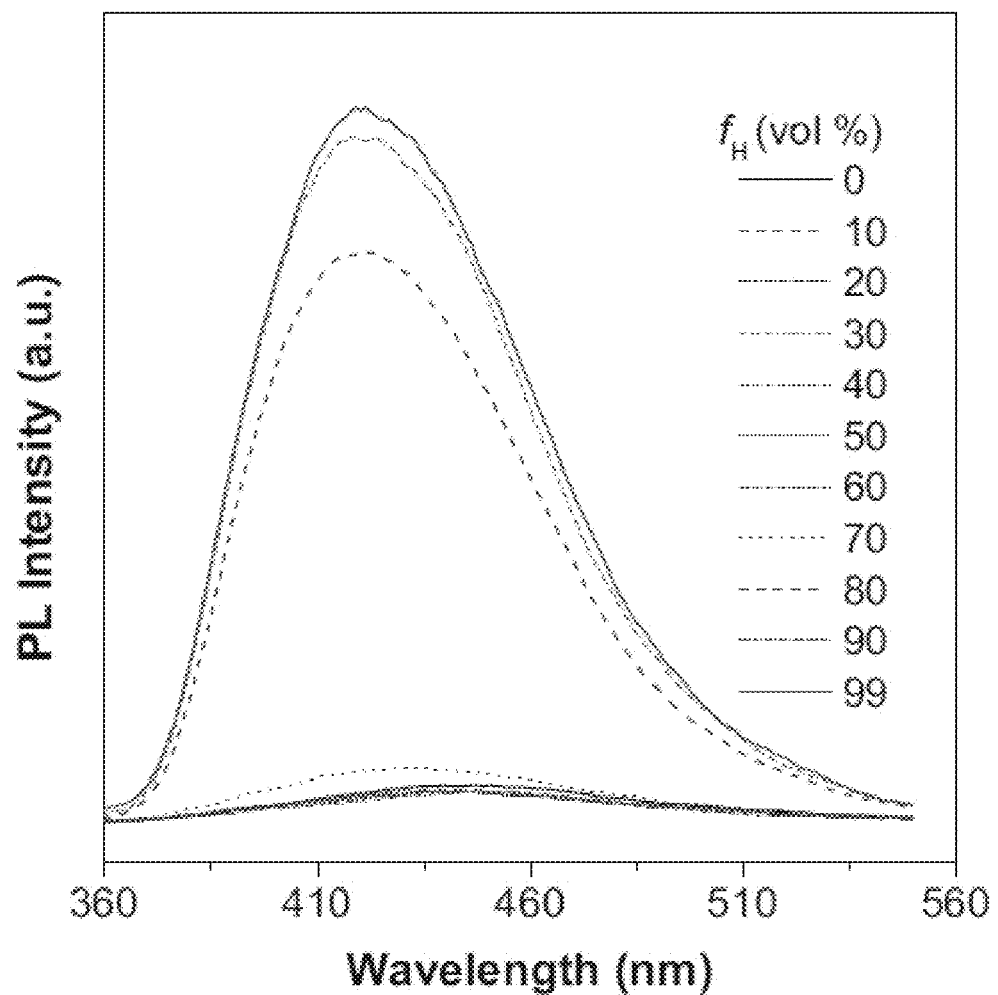
FIG. 6 depicts PL spectra of TPO in THF/hexane mixtures with different hexane fractions ($f_H$) (excitation at 350 nm).
Figure 7:
FIG. 7 depicts fluorescent photographs of TPO in THF/hexane mixtures with different $f_H$ taken under 365 nm UV irradiation (concentration: 10 μM).
Figure 8:
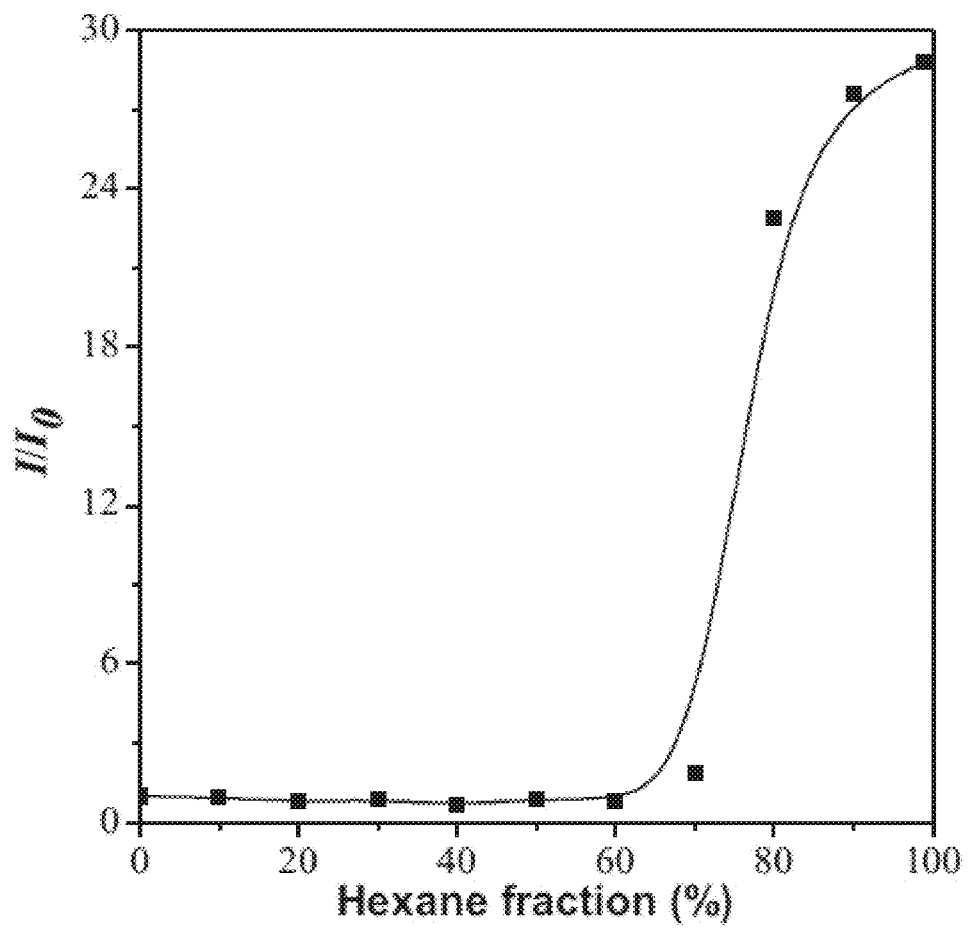
FIG. 8 depicts a plot of relative PL intensity ($I/I_0$) versus the composition of the THF/hexane mixtures of TPO. $I_0$=PL intensity in pure THF.

FIG. 5 depicts the absorption spectrum of TPO in ethanol. FIG. 6 depicts PL spectra of TPO in THF/hexane mixtures with different hexane fractions (f$_H$) (excitation at 350 nm). FIG. 7 depicts fluorescent photographs of TPO in THF/hexane mixtures with different f$_H$ taken under 365 nm UV irradiation (concentration: 10 μM). FIG. 8 depicts a plot of relative PL intensity (I/I$_0$) versus the composition of the THF/hexane mixtures of TPO. I$_0$=PL intensity in pure THF.

Example 3

Synthesis and Characterization of 1MOTPO

An exemplary reaction scheme for preparing 1MOTPO is provided below:

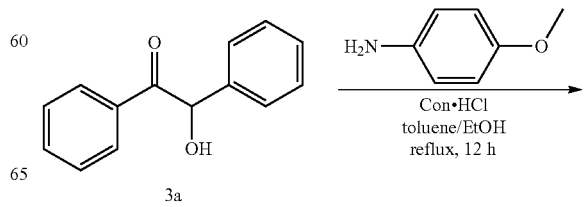

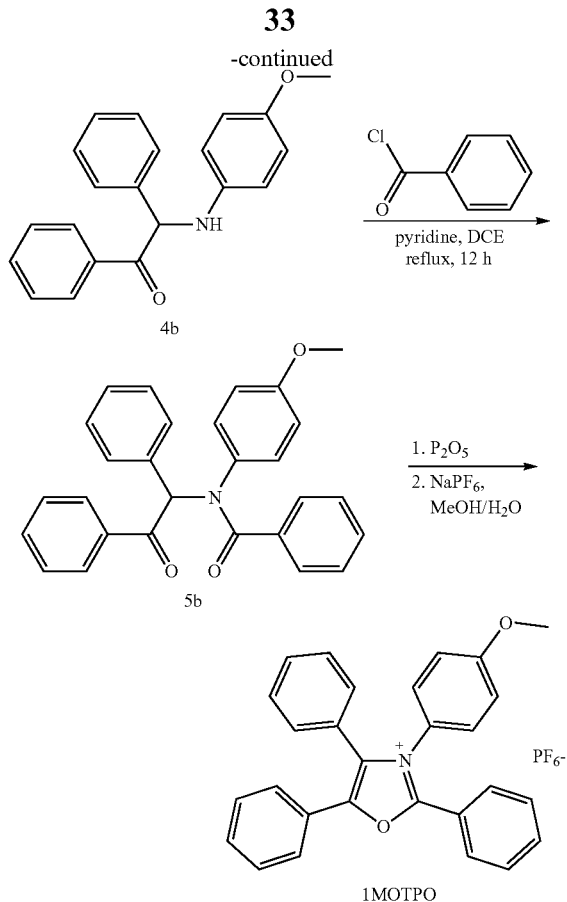

4b

5b

1MOTPO

Synthesis of Compound 4b

To a solution of 3a (2.12 g, 10.00 mmol) and 4-Methoxyaniline (1.48 g, 12.00 mmol) in toluene:EtOH=10:1 (40 mL) were added ten drops of concentrated HCl. The reaction mixture was stirred and refluxed for 12 h. After cooling the reaction mixture to room temperature, the precipitate was filtered under vacuum. The solid was added to ethyl acetate and $K_2CO_3$ solution. The aqueous phase was extracted with ethyl acetate. The combined organic layers were washed with brine, dried over anhydrous sodium sulfate and concentrated under reduced pressure. The residue was purified by flash column chromatography with Hexane/EA (10:1-2:1, v/v) to afford the desired compound 4b as light white solid (2.54 g, 80%). $^1$H NMR (400 MHz, Acetone) δ 8.14-8.08 (m, 2H), 7.56-7.49 (m, 3H), 7.43 (dd, J=10.5, 4.7 Hz, 2H), 7.23 (dd, J=10.4, 4.8 Hz, 2H), 7.17-7.10 (m, 1H), 6.77-6.69 (m, 2H), 6.67-6.59 (m, 2H), 6.27 (d, 7=8.1 Hz, 1H), 5.51 (d, 7=8.1 Hz, 1H), 3.59 (s, 3H). $^{13}$C NMR (101 MHz, Acetone) δ 196.77, 151.52, 140.31, 138.01, 134.84, 132.74, 128.18, 128.05, 128.02, 127.71, 127.06, 114.25, 113.82, 61.94, 54.20. HRMS (MALDI-TOF) m/z: [M]$^+$ calcd for $C_{21}H_{19}NO_2$, 317.1416, found, 317.1349.

Synthesis of Compound 5b

Benzoyl chloride (1.09 mL, 9.45 mmol) was added to a solution of 4b (2.00 g, 6.30 mmol) and pyridine (1.49 mL, 18.90 mmol) in 1, 2-dichloroethane (30 mL) and refluxed under nitrogen for 12 h. The reaction mixture was cooled to room temperature and washed with $Na_2CO_3$ solution (3×30 mL). The organic layer was dried over sodium sulfate. After evaporation of the solvent under vacuum, the residue was subjected to flash column chromatography with hexane/EA (20:1, v/v) to give white solid 5b (2.34 g, 88%). $^1$H NMR (400 MHz, Acetone) δ 8.02 (d, J=8.8 Hz, 2H), 7.54-7.38 (m, 4H), 7.28-7.22 (m, 3H), 7.21-7.17 (m, 2H), 7.16-7.11 (m, 5H), 6.93 (d, J=5.9 Hz, 2H), 6.48 (d, J=9.1 Hz, 2H), 3.55 (s, 3H). $^{13}$C NMR (101 MHz, Acetone) δ 195.23, 169.64, 136.30, 135.61, 133.27, 132.71, 132.24, 131.85, 130.53, 128.91, 128.38, 127.95, 127.91, 127.85, 127.68, 127.63, 126.87, 112.37, 66.65, 53.95. HRMS (MALDI-TOF) m/z: [M+H]$^+$ calcd for $C_{28}H_{24}NO_3$, 422.1756, found, 422.1745.

Synthesis of 1MOTPO

Compound 5b (0.50 g, 1.19 mmol) and phosphorus pentoxide (0.20 g, 1.42 mmol) were dissolved in dry DCM (1.0 mL) and heated under nitrogen at 180° C. for 4 h. The reaction mixture was cooled to −20° C. The solution of $NaPF_6$ (1.00 g, 5.95 mmol) in $H_2O$ and acetone (10 mL) was added to the reaction mixture and stirred at −20° C. for 30 min. The mixture was slowly warmed to room temperature and stirred for 2 h. Acetone was removed under vacuum. The solid was filtered, washed with water and purified by flash column chromatography (DCM: Methanol=1:0-10:1) to afford the desired compound 1MOTPO (490 mg, 75%). $^1$H NMR (400 MHz, MeOD) δ 7.79-7.75 (dt, J=8.9, 3.4 Hz, 3H), 7.68-7.63 (m, 2H), 7.60-7.56 (m, 2H), 7.54-7.43 (m, 10H), 7.05 (d, J=9.1 Hz, 2H), 3.82 (s, 3H). $^{13}$C NMR (101 MHz, MeOD) δ 161.47, 158.96, 147.76, 134.12, 130.52, 130.41, 130.33, 130.27, 128.92, 128.69, 128.59, 128.40, 127.86, 125.42, 123.80, 123.18, 122.44, 119.67, 114.64, 54.26. HRMS (MALDI-TOF) m/z: [M-PF$_6$]$^+$ calcd for $C_{28}H_{22}NO_2^+$, 404.1645, found, 404.1619.

Figure 9:
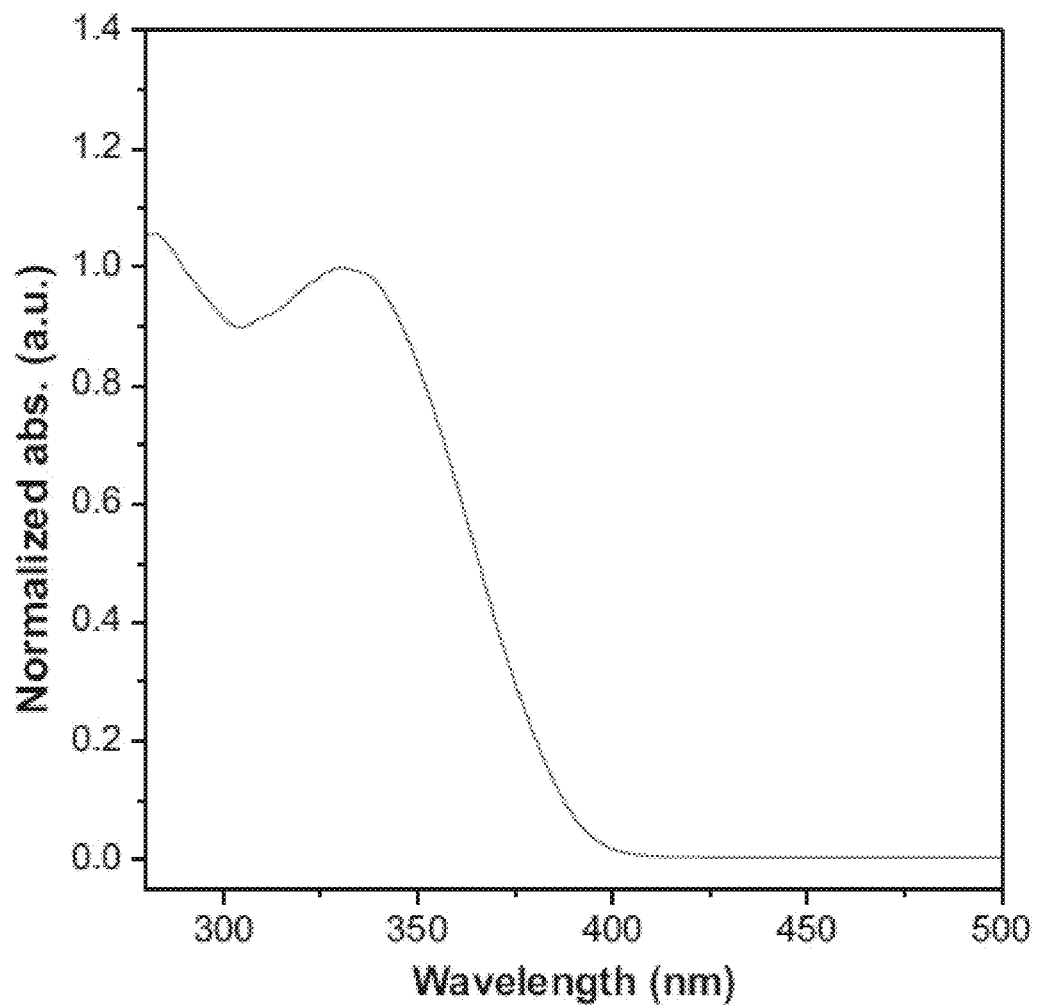
FIG. 9 depicts the absorption spectrum of 1MOTPO in ethanol.
Figure 10:
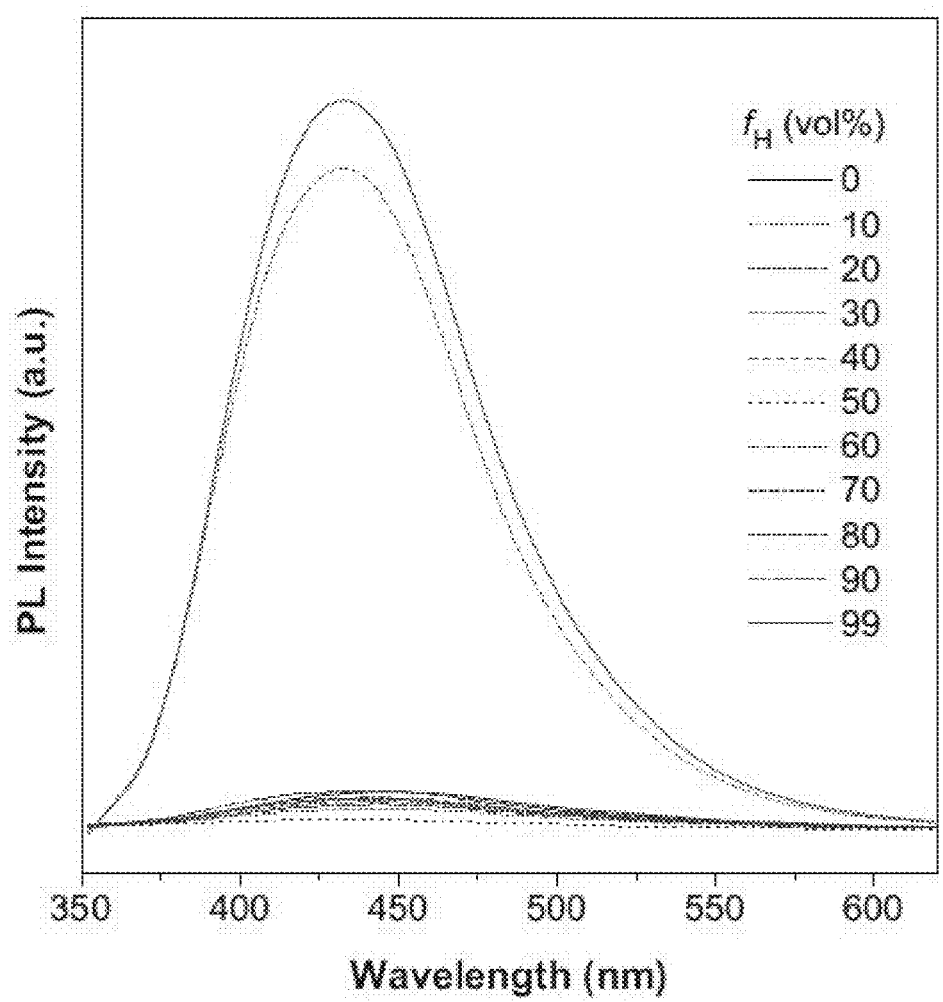
FIG. 10 depicts PL spectra of 1MOTPO in THF/hexane mixtures with different hexane fractions ($f_H$) (excitation at 350 nm).
Figure 11:
FIG. 11 depicts fluorescent photographs of 1MOTPO in THF/hexane mixtures with different $f_H$ taken under 365 nm UV irradiation (concentration: 10 μM).
Figure 12:
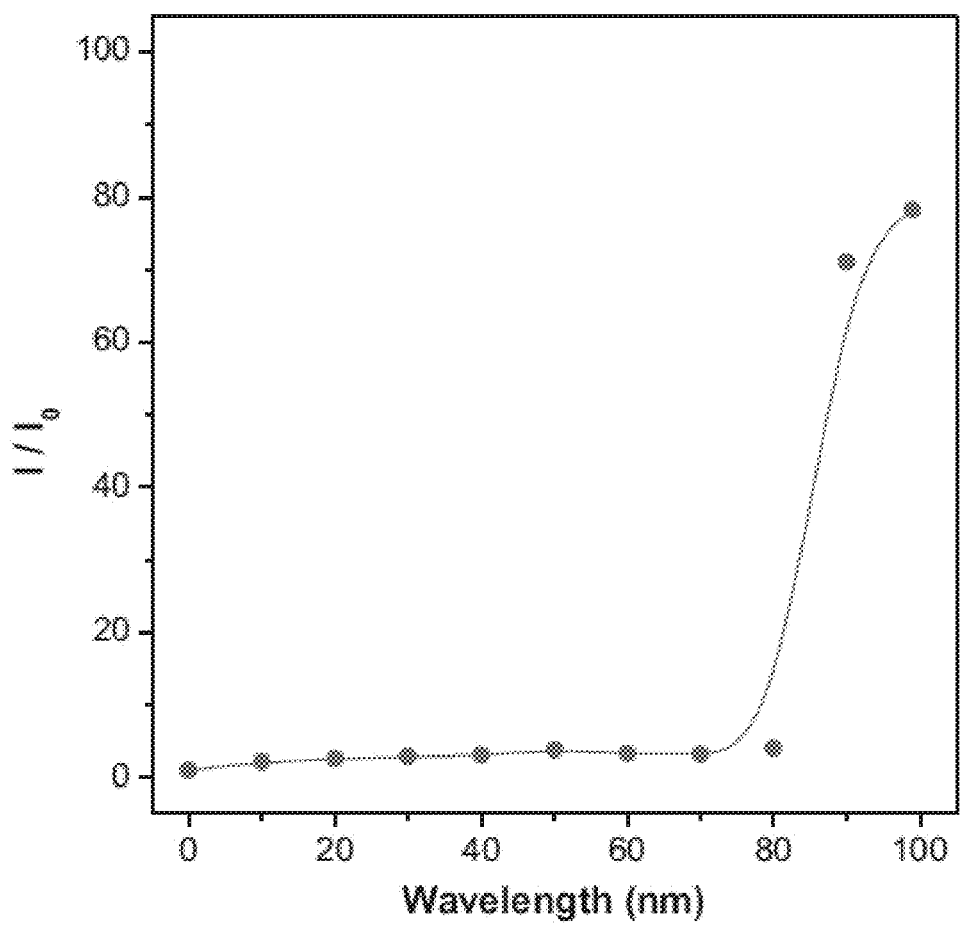
FIG. 12 depicts a plot of relative PL intensity ($I/I_0$) versus the composition of the THF/hexane mixtures of 1MOTPO. $I_0$=PL intensity in pure THF.

FIG. 9 depicts the absorption spectrum of 1MOTPO in ethanol. FIG. 10 depicts PL spectra of 1MOTPO in THF/hexane mixtures with different hexane fractions (fa) (excitation at 350 nm). FIG. 11 depicts fluorescent photographs of 1MOTPO in THF/hexane mixtures with different fa taken under 365 nm UV irradiation (concentration: 10 μM). FIG. 12 depicts a plot of relative PL intensity ($I/I_0$) versus the composition of the THF/hexane mixtures of 1MOTPO. $I_0$=PL intensity in pure THF.

Example 4

Synthesis and Characterization of 2MOTPO

An exemplary reaction scheme for preparing 2MOTPO is as provided below:

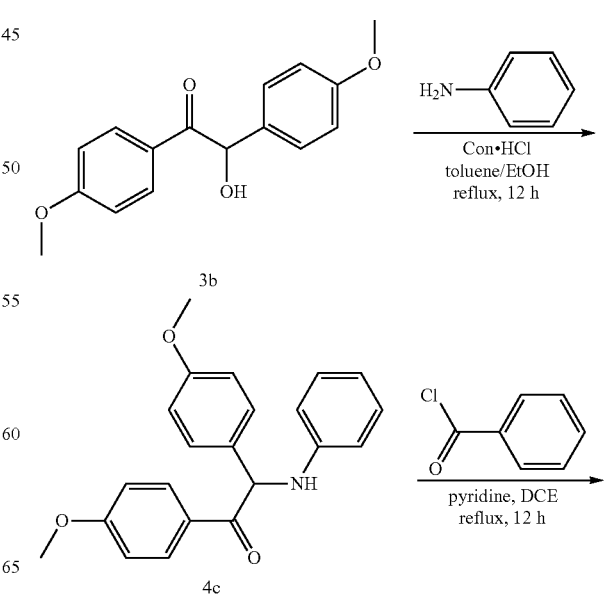

3b

4c

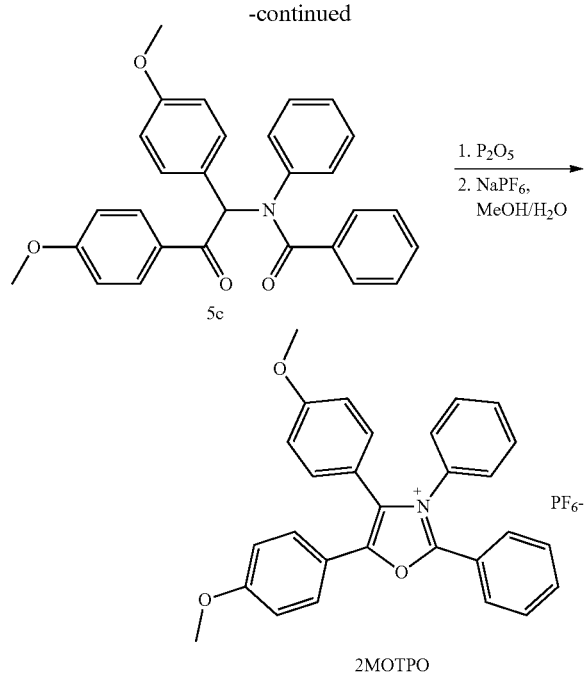

Synthesis of Compound 4c

To a solution of 3b (2.72 g, 10.00 mmol) and aniline (1.12 g, 12.00 mmol) in toluene:EtOH=10:1 (40 mL) were added ten drops of concentrated HCl. The reaction mixture was stirred and refluxed for 12 h. After cooling the reaction mixture to room temperature, the precipitate was filtered under vacuum. The solid was added to ethyl acetate and $K_2CO_3$ solution. The aqueous phase was extracted with ethyl acetate. The combined organic layers were washed with brine, dried over anhydrous sodium sulfate and concentrated under reduced pressure. The residue was purified by flash column chromatography with Hexane/EA (10:1-2:1, v/v) to afford the desired compound 4c as light white solid (3.09 g, 89%). $^1$H NMR (400 MHz, MeOD) δ 7.99 (d, J=8.8 Hz, 2H), 7.46-7.43 (m, 3H), 7.36-7.33 (m, 2H), 7.29 (d, J=8.6 Hz, 2H), 6.94 (d, J=8.9 Hz, 2H), 6.90 (d, J=8.6 Hz, 2H), 6.46 (s, 1H), 3.80 (s, 3H), 3.74 (s, 3H). $^{13}$C NMR (101 MHz, MeOD) δ 189.95, 164.24, 160.73, 133.10, 130.91, 130.17, 129.26, 128.98, 128.83, 123.21, 122.11, 114.04, 113.24, 69.55, 54.20, 53.86. HRMS (MALDI-TOF) m/z: [M+H]$^+$ calcd for $C_{22}H_{22}NO_3^+$, 348.1600, found, 348.1592.

Synthesis of Compound 5c

Benzoyl chloride (0.99 mL, 8.63 mmol) was added to a solution of 4c (2.00 g, 5.76 mmol) and pyridine (1.36 mL, 17.28 mmol) in 1, 2-dichloroethane (30 mL) and refluxed under nitrogen for 12 h. The reaction mixture was cooled to room temperature and washed with $Na_2CO_3$ solution (3×30 mL). The organic layer was dried over sodium sulfate. After evaporation of the solvent under vacuum, the residue was subjected to flash column chromatography with hexane/EA (20:1, v/v) to give white solid 5c (2.03 g, 78%). NMR (400 MHz, MeOD) δ 8.00 (d, J=8.9 Hz, 2H), 7.28-7.24 (m, 3H), 7.23-7.05 (m, 4H), 7.02 (d, J=8.8 Hz, 3H), 6.96-6.93 (m, 3H), 6.90 (d, J=9.0 Hz, 2H), 6.65 (d, J=8.8 Hz, 2H), 3.79 (s, 3H), 3.62 (s, 3H). $^{13}$C NMR (101 MHz, MeOD) δ 194.04, 171.18, 163.10, 159.19, 139.43, 135.64, 131.54, 130.76, 130.25, 128.45, 127.62, 127.19, 127.05, 126.73, 126.28, 124.38, 113.02, 112.78, 66.24, 53.98, 53.55. HRMS (MALDI-TOF) m/z: [M+Na]$^+$ calcd for $C_{29}H_5NNaO_4$, 474.1681, found, 474.1691.

Synthesis of 2MOTPO

Compound 5c (0.50 g, 1.11 mmol) and phosphorus pentoxide (0.19 g, 1.33 mmol) were dissolved in dry DCM (1.0 mL) and heated under nitrogen at 180° C. for 4 h. The reaction mixture was cooled to −20° C. The solution of $NaPF_6$ (0.93 g, 5.55 mmol) in $H_2O$ and acetone (10 mL) was added to the reaction mixture and stirred at −20° C. for 30 min. The mixture was slowly warmed to room temperature and stirred for 2 h. Acetone was removed under vacuum. The solid was filtered, washed with water and purified by flash column chromatography (DCM:Methanol=1:0-10:1) to afford the desired compound 2MOTPO (418 mg, 75%). $^1$H NMR (400 MHz, MeOD) δ 7.73-7.71 (m, 2H), 7.68 (d, J=7.5 Hz, 2H), 7.61-7.49 (m, 8H), 7.30 (d, J=8.8 Hz, 2H), 7.00 (d, J=9.0 Hz, 2H), 6.94 (d, J=8.8 Hz, 2H), 3.84 (s, 3H), 3.80 (s, 3H). $^{13}$C NMR (101 MHz, DMSO) δ 161.21, 160.95, 157.64, 148.18, 134.40, 131.87, 131.42, 130.87, 130.08, 129.05, 128.90, 128.52, 127.27, 126.54, 119.36, 115.75, 114.44, 114.33, 113.42, 54.90, 54.74. HRMS (MALDI-TOF) m/z: [M-PF$_6$]$^+$ calcd for $C_{29}H_{24}NO_3^+$, 434.1751, found, 434.1776.

Figure 13:
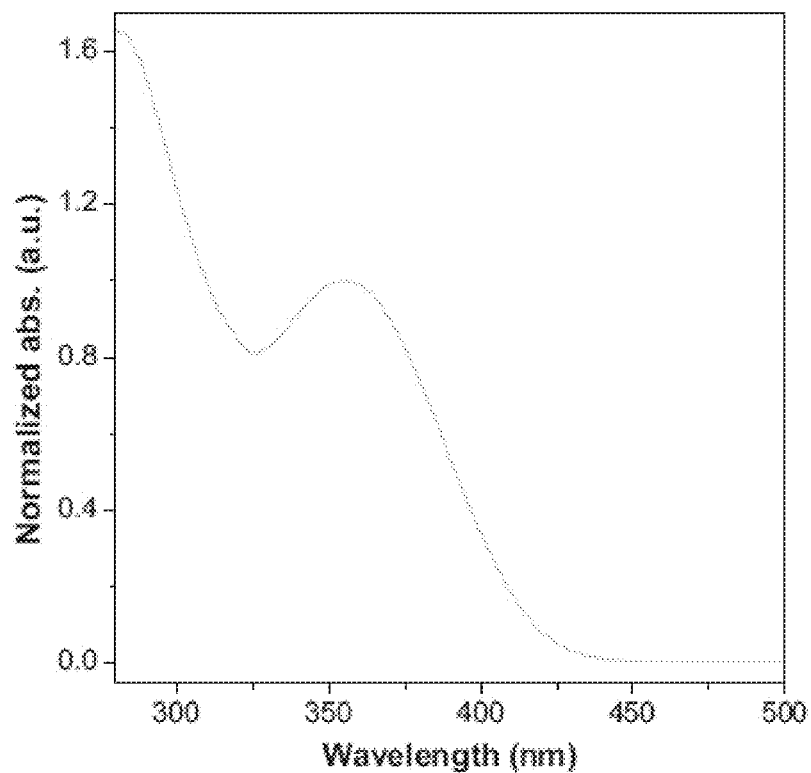
FIG. 13 depicts the absorption spectrum of 2MOTPO in ethanol.
Figure 14:
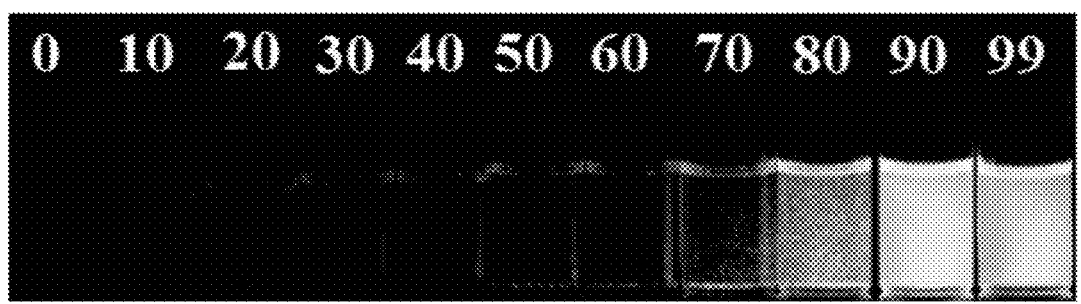
FIG. 14 depicts fluorescent photographs of 2MOTPO in THF/hexane mixtures with different $f_H$ taken under 365 nm UV irradiation (concentration: 10 μM).
Figure 15:
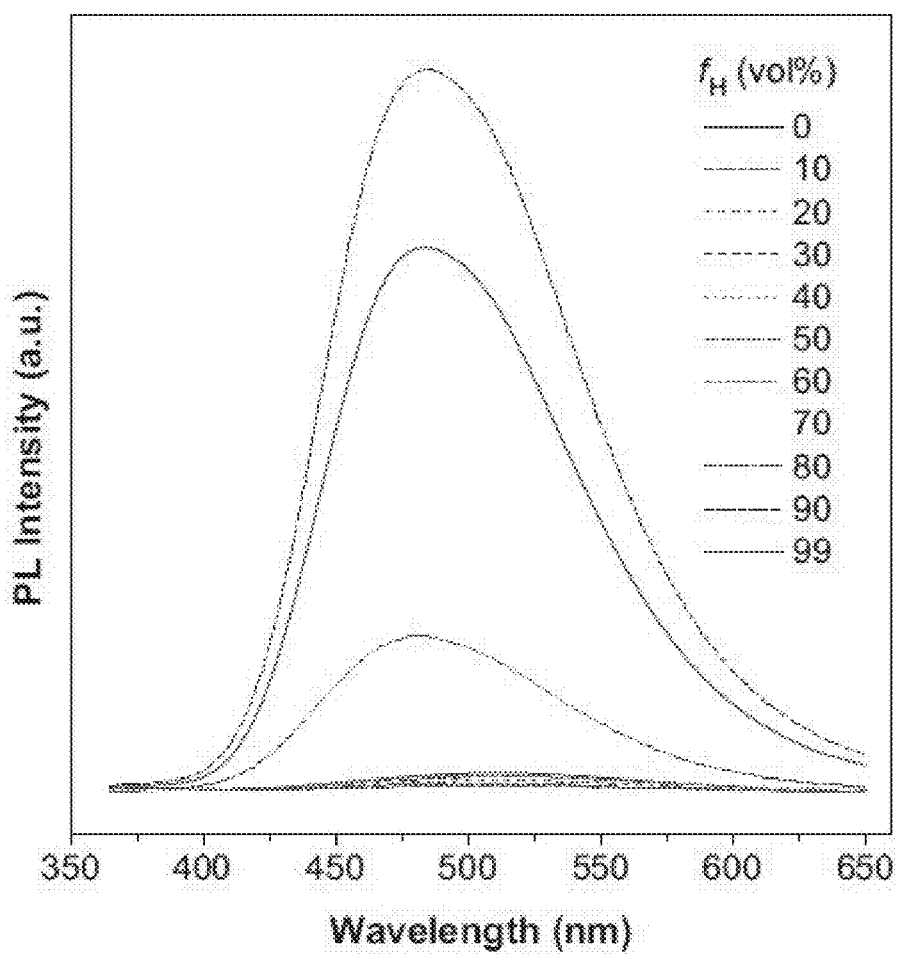
FIG. 15 depicts PL spectra of 2MOTPO in THF/hexane mixtures with different hexane fractions ($f_H$) (excitation at 370 nm).
Figure 16:
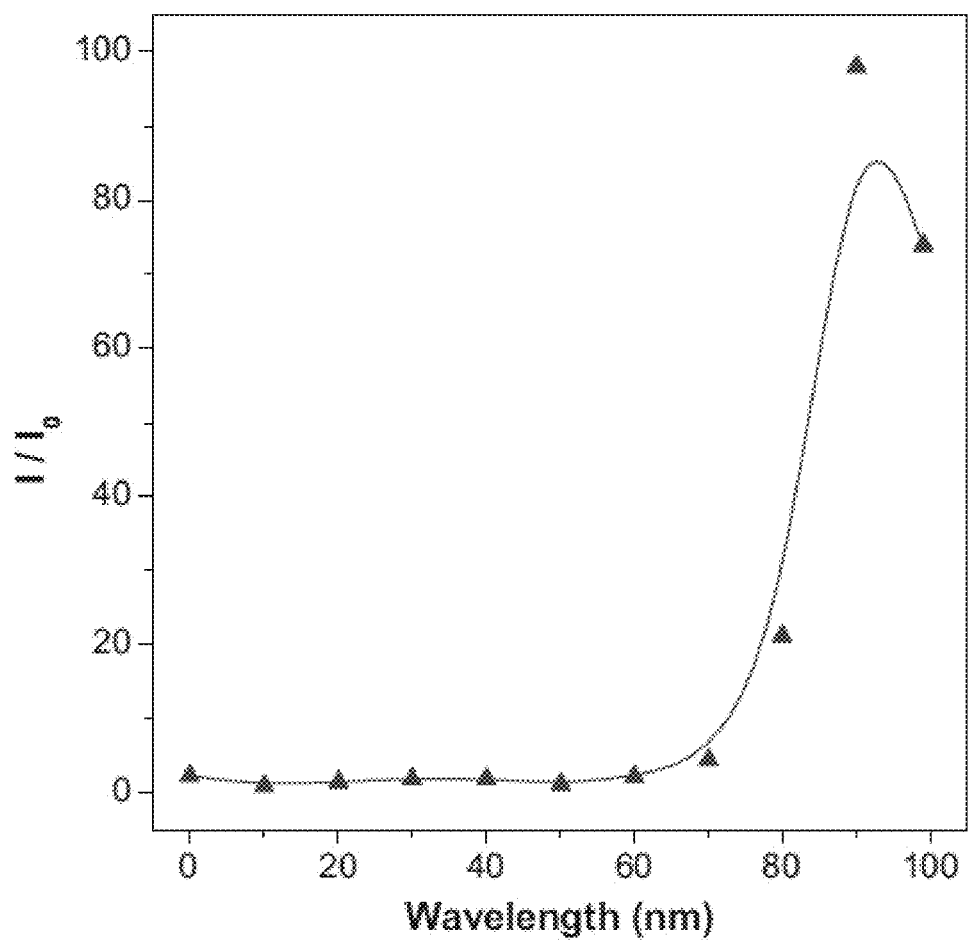
FIG. 16 depicts a plot of relative PL intensity ($I/I_0$) versus the composition of the THF/hexane mixtures of 2MOTPO ($I_0$=PL intensity in pure THF).

FIG. 13 is depicts the absorption spectrum of 2MOTPO in ethanol ito. FIG. 14 depicts fluorescent photographs of 2MOTPO in THF/hexane mixtures with different $f_H$ taken under 365 nm UV irradiation (concentration: 10 μM). FIG. 15 depicts PL spectra of 2MOTPO in THF/hexane mixtures with different hexane fractions ($f_H$) (excitation at 370 nm). FIG. 16 depicts a plot of relative PL intensity (I/I$_0$) versus the composition of the THF/hexane mixtures of 2MOTPO (I$_0$=PL intensity in pure THF).

Example 5

Synthesis and Characterization of 3MOTPO

An exemplary reaction scheme for preparing 3MOTPO is as provided below:

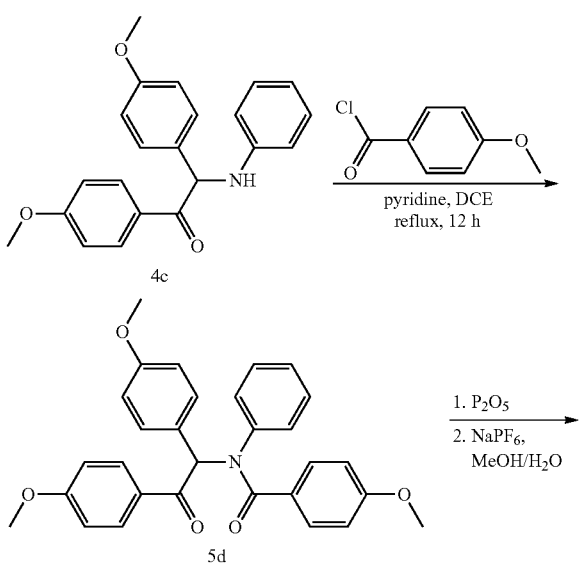

-continued

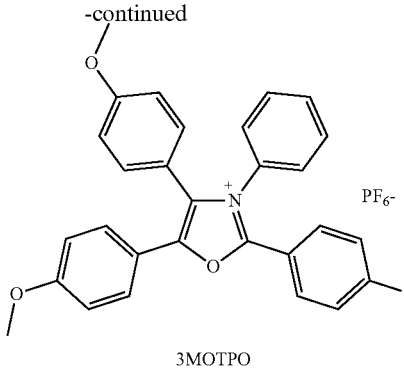

3MOTPO

Synthesis of compound 5d

4-Methoxybenzoyl chloride (1.47 g, 8.63 mmol) was added to a solution of 4c (2.00 g, 5.76 mmol) and pyridine (1.36 mL, 17.28 mmol) in 1, 2-dichloroethane (30 mL) and refluxed under nitrogen for 12 h. The reaction mixture was cooled to room temperature and washed with Na$_2$CO$_3$ solution (3×30 mL). The organic layer was dried over sodium sulfate. After evaporation of the solvent under vacuum, the residue was subjected to flash column chromatography with hexane/EA (20:1, v/v) to give white solid 5d (2.22 g, 80%). $^1$H NMR (400 MHz, MeOD) δ 7.97 (d, J=8.8 Hz, 2H), 7.22 (d, J=8.8 Hz, 2H), 7.20 (s, 1H), 7.07-6.91 (m, 7H), 6.87 (d, J=8.8 Hz, 2H), 6.634 (d, J=8.8 Hz, 2H), 6.629 (d, J=8.4 Hz, 2H), 3.77 (s, 3H), 3.65 (s, 3H), 3.62 (s, 3H). $^{13}$C NMR (101 MHz, MeOD) δ 194.30, 170.77, 163.01, 160.03, 159.13, 139.88, 131.52, 130.63, 130.26, 129.55, 127.68, 127.29, 127.18, 126.25, 124.56, 113.12, 112.85, 112.04, 66.32, 54.12, 53.79, 53.74. HRMS (MALDI-TOF) m/z: [M+H]$^+$ calcd for C$_{30}$H$_{28}$NO$_5$, 482.1967, found, 482.1906.

Synthesis of 3MOTPO

Compound 5d (0.50 g, 1.04 mmol) and phosphorus pentoxide (0.18 g, 1.25 mmol) were dissolved in dry DCM (1.0 mL) and heated under nitrogen at 180° C. for 4 h. The reaction mixture was cooled to −20° C. The solution of NaPF$_6$ (0.87 g, 5.20 mmol) in H$_2$O and acetone (10 mL) was added to the reaction mixture and stirred at −20° C. for 30 min. The mixture was slowly warmed to room temperature and stirred for 2 h. Acetone was removed under vacuum. The solid was filtered, washed with water and purified by flash column chromatography (DCM:Methanol=1:0-10:1) to afford the desired compound 3MOTPO (443 mg, 70%). $^1$H NMR (400 MHz, MeOD) δ 7.66 (d, J=9.0 Hz, 2H), 7.60-7.55 (m, 7H), 7.33 (d, J=8.7 Hz, 2H), 7.07 (d, J=9.0 Hz, 2H), 7.02 (d, J=8.9 Hz, 2H), 6.96 (d, J=8.7 Hz, 2H), 3.89 (s, 3H), 3.84 (s, 3H), 3.79 (s, 3H). $^{13}$C NMR (101 MHz, MeOD) δ 164.43, 161.23, 161.18, 158.05, 147.21, 131.99, 131.59, 130.99, 130.92, 129.70, 128.04, 126.97, 126.74, 116.25, 114.24, 114.11, 113.90, 113.78, 111.39, 54.48, 53.98, 53.86. HRMS (MALDI-TOF) m/z: [M-PF$_6$]$^+$ calcd for C$_{30}$H$_{26}$NO$_4^+$, 464.1856, found, 464.1870.

Figure 17:
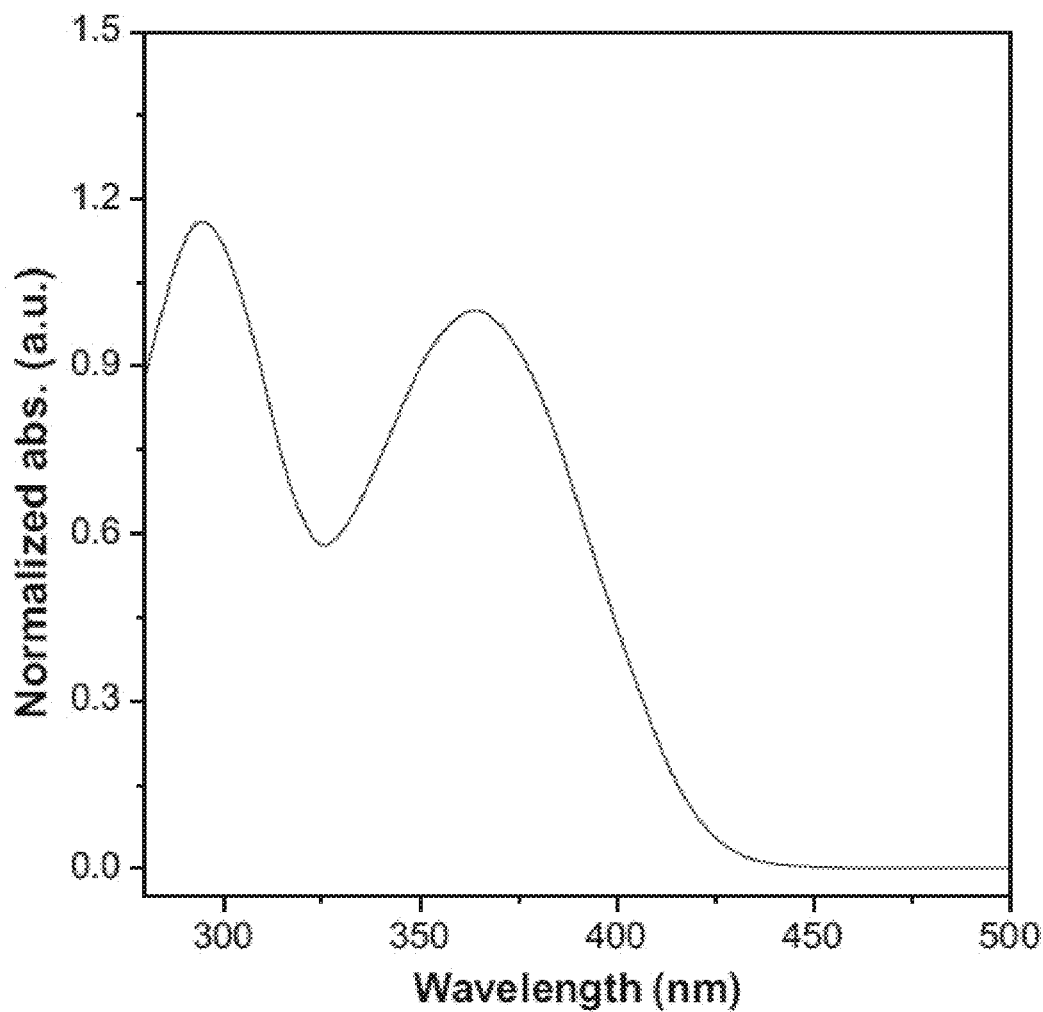
FIG. 17 depicts the absorption spectrum of 3MOTPO in ethanol.
Figure 18:
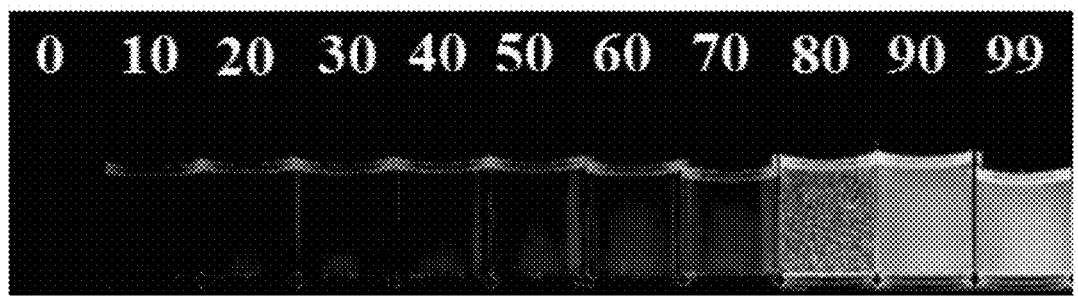
FIG. 18 depicts fluorescent photographs of 3MOTPO in THF/hexane mixtures with different $f_H$ taken under 365 nm UV irradiation (concentration: 10 μM).
Figure 19:
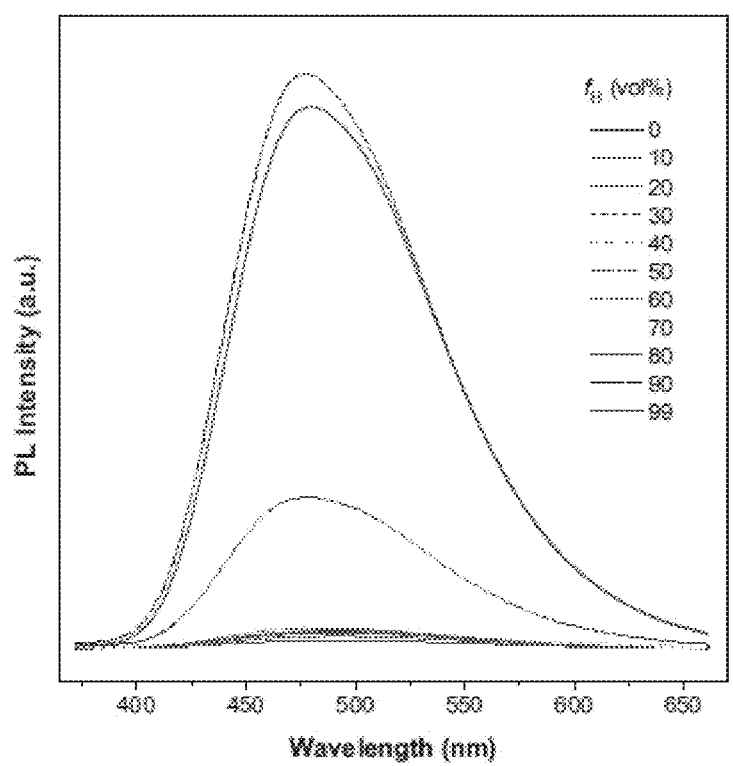
FIG. 19 depicts PL spectra of 3MOTPO in THF/hexane mixtures with different hexane fractions ($f_H$) (excitation at 370 nm).
Figure 20:
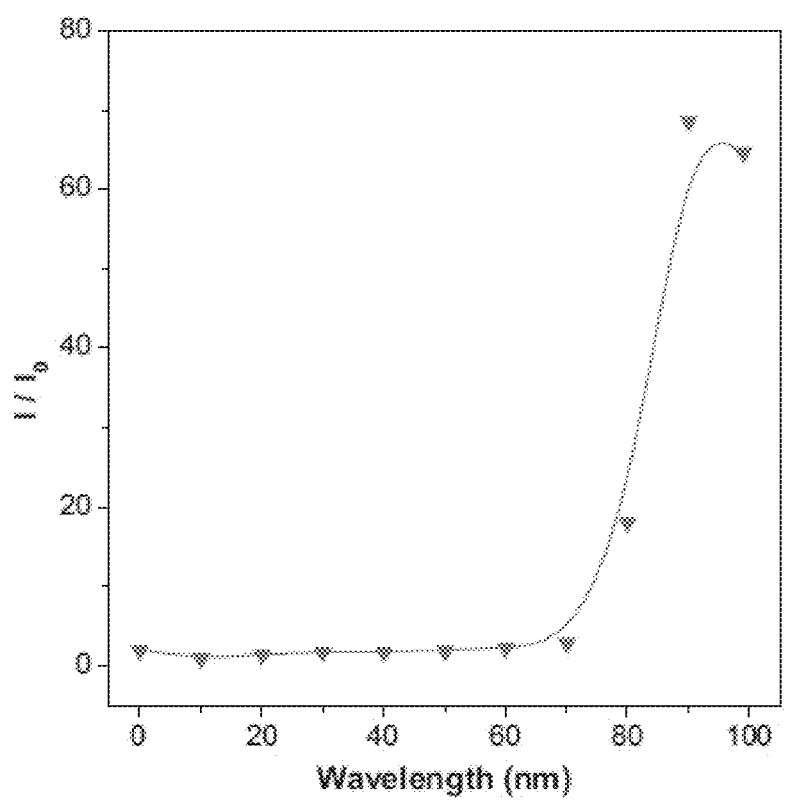
FIG. 20 depicts a plot of relative PL intensity ($I/I_0$) versus the composition of the THF/hexane mixtures of 3MOTPO ($I_0$=PL intensity in pure THF).

FIG. 17 depicts the absorption spectrum of 3MOTPO in ethanol. FIG. 18 depicts fluorescent photographs of 3MOTPO in THF/hexane mixtures with different f$_H$ taken under 365 nm UV irradiation (concentration: 10 μM). FIG. 19 depicts PL spectra of 3MOTPO in THF/hexane mixtures with different hexane fractions (fa) (excitation at 370 nm). FIG. 20 depicts a plot of relative PL intensity (I/I$_0$) versus the composition of the THF/hexane mixtures of 3MOTPO (I$_0$=PL intensity in pure THF).

Example 6

Synthesis and Characterization of 4MOTPO

An exemplary reaction scheme for preparing 4MOTPO is as provided below:

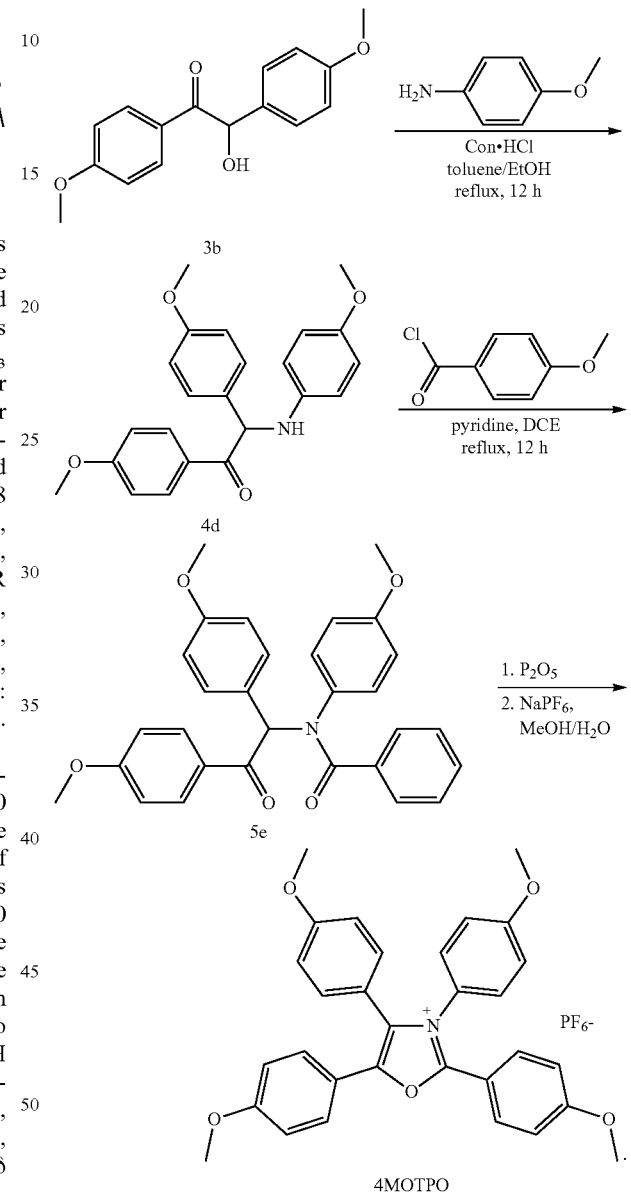

Synthesis of Compound 4d

To a solution of 3b (2.72 g, 10.00 mmol) and 4-Methoxyaniline (1.48 g, 12.00 mmol) in toluene:EtOH=10:1 (40 mL) were added ten drops of concentrated HCl. The reaction mixture was stirred and refluxed for 12 h. After cooling the reaction mixture to room temperature, the precipitate was filtered under vacuum. The solid was added to ethyl acetate and K$_2$CO$_3$ solution. The aqueous phase was extracted with ethyl acetate. The combined organic layers were washed with brine, dried over anhydrous sodium sulfate and concentrated under reduced pressure. The residue was purified by flash column chromatography with Hexane/EA (10:1-2:1, v/v) to afford the desired compound 4d as light white solid (2.87 g, 76%). NMR (400 MHz, MeOD) δ 7.98 (d, J=9.0 Hz, 2H), 7.31 (d, J=8.8 Hz, 2H), 7.27 (d, J=9.0 Hz, 2H), 6.95 (d, J=9.1 Hz, 2H), 6.92 (d, J=6.1 Hz, 2H), 6.90 (d, J=5.9 Hz, 2H), 6.40 (s, 1H), 3.79 (s, 3H), 3.76 (s, 3H), 3.73 (s, 3H). $^{13}$C NMR (101 MHz, MeOD) δ 190.06, 164.20, 160.71, 159.82, 130.90, 130.23, 125.24, 125.22, 124.56, 121.22, 114.05, 113.95, 113.24, 69.70, 54.21, 54.12, 53.88. HRMS (MALDI-TOF) m/z: [M+H]$^+$ calcd for $C_{23}H_{24}NO_4^+$, 378.1705, found, 378.1720.

Synthesis of compound 5e

4-Methoxybenzoyl chloride (1.47 g, 8.63 mmol) was added to a solution of 4d (2.17 g, 5.76 mmol) and pyridine (1.36 mL, 17.28 mmol) in 1, 2-dichloroethane (30 mL) and refluxed under nitrogen for 12 h. The reaction mixture was cooled to room temperature and washed with $Na_2CO_3$ solution (3×30 mL). The organic layer was dried over sodium sulfate. After evaporation of the solvent under vacuum, the residue was subjected to flash column chromatography with hexane/EA (20:1, v/v) to give white solid 5e (2.36 g, 80%). $^1$H NMR (400 MHz, MeOD) δ 7.99 (d, J=8.9 Hz, 2H), 7.23 (d, J=8.9 Hz, 2H), 7.18 (s, 1H), 7.01 (d, J=8.7 Hz, 2H), 6.90 (d, J=8.9 Hz, 2H), 6.67 (d, J=8.5 Hz, 4H), 6.51 (d, J=8.1 Hz, 2H), 3.79 (s, 3H), 3.68 (s, 3H), 3.64 (s, 3H), 3.59 (s, 3H). $^{13}$C NMR (101 MHz, MeOD) δ 194.28, 171.01, 163.04, 159.99, 159.18, 157.81, 132.50, 131.64, 131.55, 130.19, 129.39, 127.74, 127.54, 124.70, 113.03, 112.74, 112.14, 111.96, 66.28, 53.96, 53.62, 53.59, 53.57. HRMS (MALDI-TOF) m/z: [M+Na]$^+$ calcd for $C_{31}H_{29}NNaO_6$, 534.1893, found, 534.1961.

Synthesis of 4MOTPO

Compound 5e (0.50 g, 0.98 mmol) and phosphorus pentoxide (0.17 g, 1.17 mmol) was dissolved in dry DCM (1.0 mL) and heated under nitrogen at 180° C. for 4 h. The reaction mixture was cooled to −20° C. The solution of $NaPF_6$ (0.82 g, 4.90 mmol) in $H_2O$ and acetone (10 mL) was added to the reaction mixture and stirred at −20° C. for 30 min. The mixture was slowly warmed to room temperature and stirred for 2 h. Acetone was removed under vacuum. The solid was filtered, washed with water and purified by flash column chromatography (DCM:Methanol=1:0-10:1) to afford the desired compound 4MOTPO (100 mg, 54%). $^1$H NMR (400 MHz, CDCl$_3$) δ 7.59 (d, J=9.0 Hz, 2H), 7.49 (d, J=8.8 Hz, 2H), 7.38 (d, J=8.9 Hz, 2H), 7.28 (d, J=8.9 Hz, 2H), 6.98-6.81 (m, 8H), 3.83 (s, 3H), 3.80 (s, 3H), 3.79 (s, 3H), 3.77 (s, 3H). $^{13}$C NMR (101 MHz, CDCl$_3$) δ 164.05, 160.85, 160.83, 160.68, 158.07, 147.93, 132.20, 131.32, 128.32, 128.04, 127.84, 123.37, 116.23, 115.13, 114.55, 114.22, 114.01, 113.95, 111.26, 55.16, 55.01, 54.78, 54.67. HRMS (MALDI-TOF) m/z: [M-PF$_6$]$^+$ calcd for $C_{31}H_{28}NO_5^+$, 494.1962, found, 494.1997.

Figure 21:
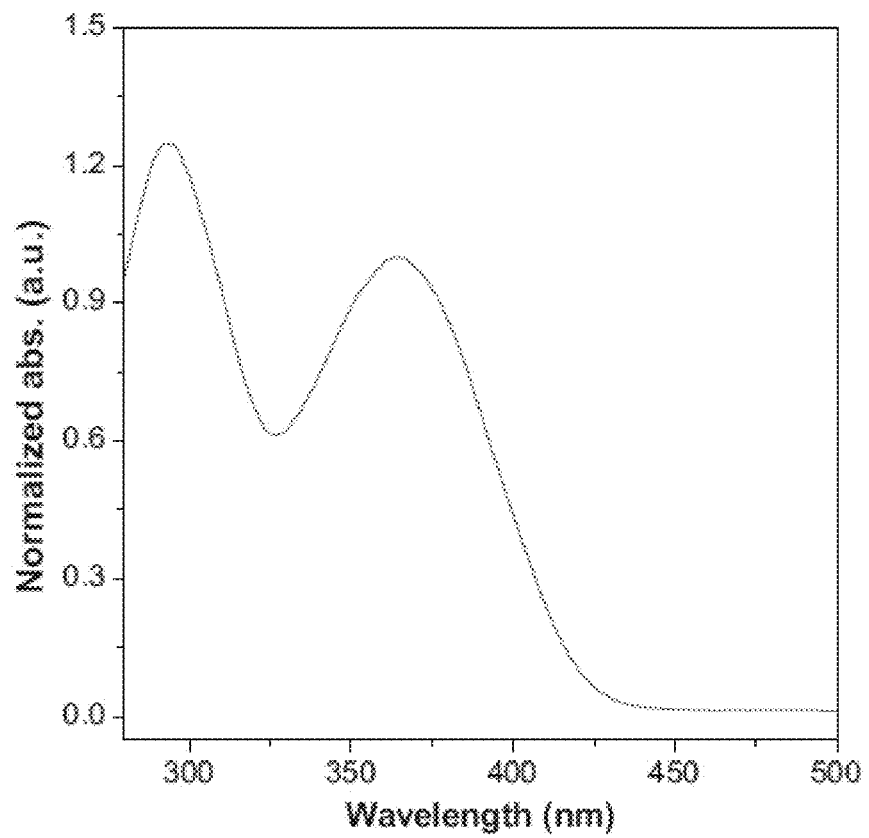
FIG. 21 depicts the absorption spectrum of 4MOTPO in ethanol.
Figure 22:
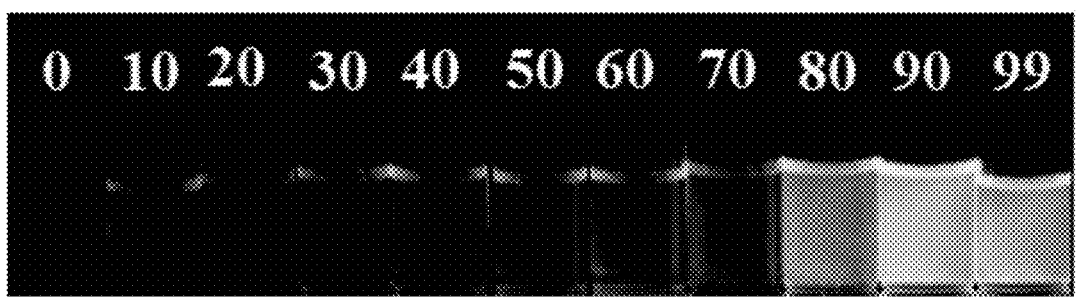
FIG. 22 depicts fluorescent photographs of 4MOTPO in THF/hexane mixtures with different $f_H$ taken under 365 nm UV irradiation (concentration: 10 μM).
Figure 23:
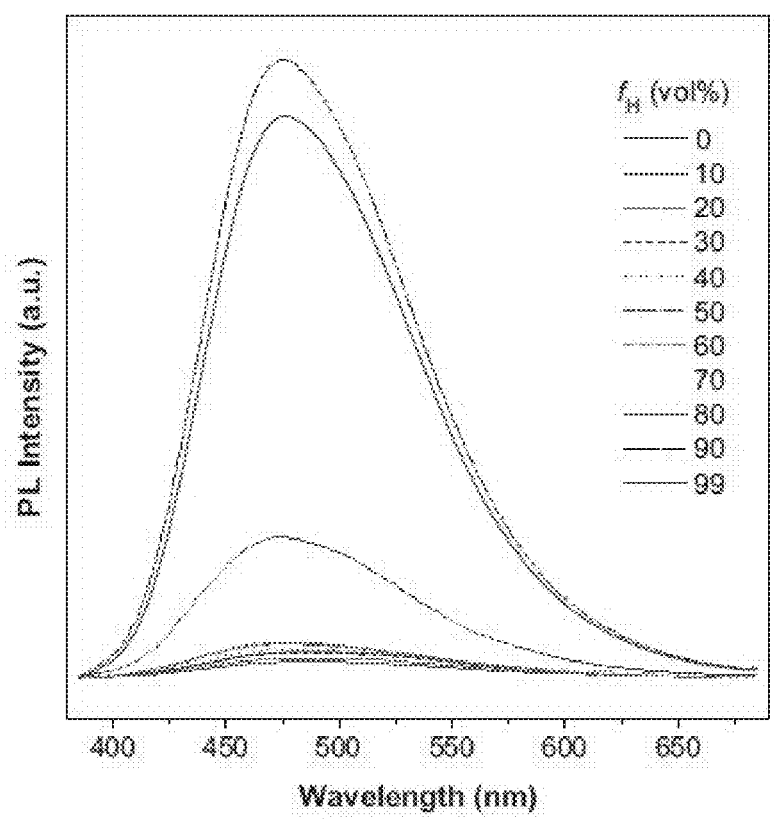
FIG. 23 depicts PL spectra of 4MOTPO in THF/hexane mixtures with different hexane fractions ($f_H$) (excitation at 370 nm).
Figure 24:
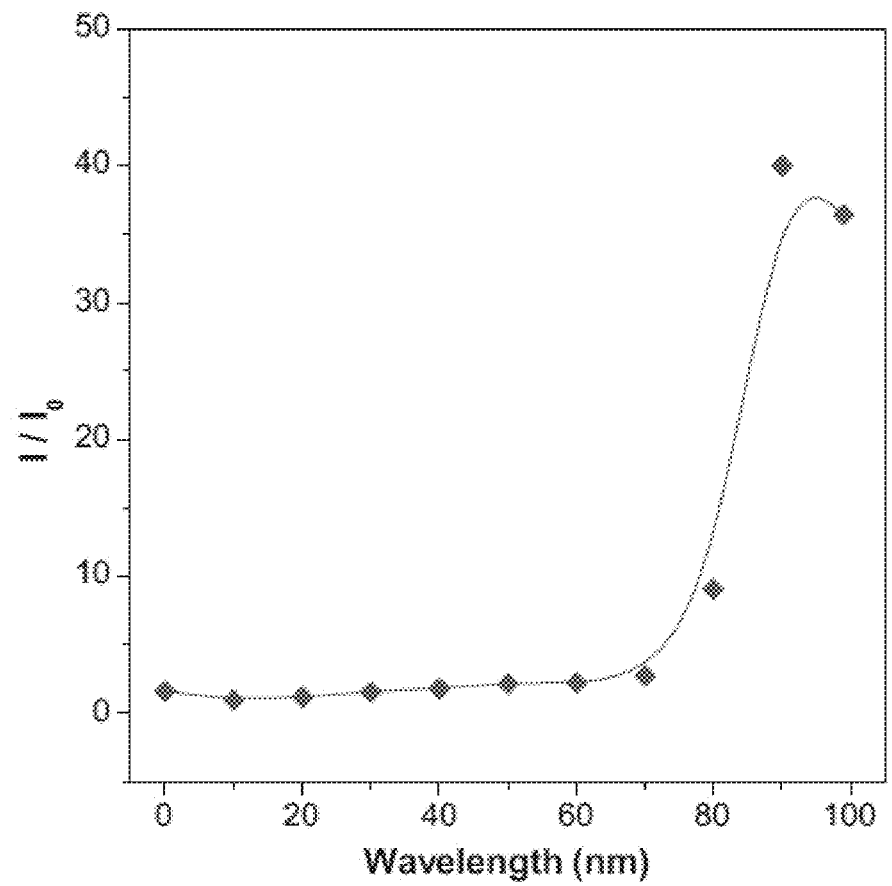
FIG. 24 depicts a plot of relative PL intensity ($I/I_0$) versus the composition of the THF/hexane mixtures of 4MOTPO. $I_0$=PL intensity in pure THF.

FIG. 21 depicts the absorption spectrum of 4MOTPO in ethanol. FIG. 22 depicts fluorescent photographs of 4MOTPO in THF/hexane mixtures with different $f_H$ taken under 365 nm UV irradiation (concentration: 10 μM). FIG. 23 depicts PL spectra of 4MOTPO in THF/hexane mixtures with different hexane fractions ($f_H$) (excitation at 370 nm). FIG. 24 depicts a plot of relative PL intensity (I/I$_0$) versus the composition of the THF/hexane mixtures of 4MOTPO. I$_0$=PL intensity in pure THF.

Example 7

Synthesis and Characterization of BrTPO

An exemplary reaction scheme for preparing BrTPO is as provided below:

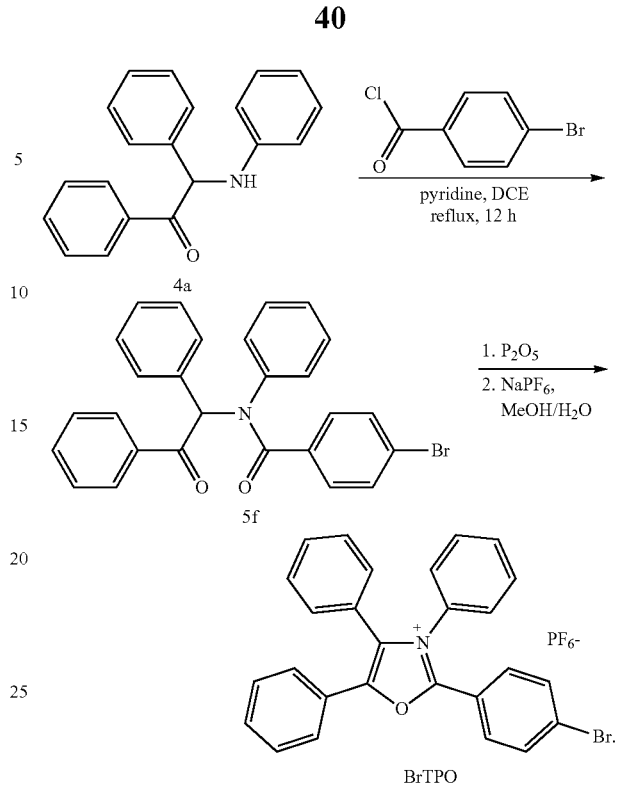

Synthesis of Compound 5f 4-bromobenzoyl chloride (1.89 g, 8.63 mmol) was added to a solution of 4a (1.66 g, 5.76 mmol) and pyridine (1.36 mL, 17.28 mmol) in 1, 2-dichloroethane (30 mL) and refluxed under nitrogen for 12 h. The reaction mixture was cooled to room temperature and washed with $Na_2CO_3$ solution (3×30 mL). The organic layer was dried over sodium sulfate. After evaporation of the solvent under vacuum, the residue was subjected to flash column chromatography with hexane/EA (20:1, v/v) to give white solid 5f (2.49 g, 92%). $^1$H NMR (400 MHz, CD2Cl2) δ 8.01 (d, J=7.2 Hz, 2H), 7.54 (t, J=7.4 Hz, 1H), 7.43 (t, J=7.6 Hz, 2H), 7.30 (d, J=8.6 Hz, 2H), 7.25 (s, 1H), 7.23-7.11 (m, 7H), 7.01 (br, 5H). $^{13}$C NMR (101 MHz, CD2Cl2) δ 195.11, 169.00, 139.47, 135.06, 134.55, 132.61, 132.47, 130.65, 130.40, 130.15, 129.51, 128.00, 127.95, 127.90, 127.54, 126.59, 122.99, 66.89.

Synthesis of BrTPO

Compound 5f (0.50 g, 1.06 mmol) and phosphorus pentoxide (0.18 g, 1.28 mmol) was dissolved in dry DCM (1.0 mL) and heated under nitrogen at 180° C. for 4 h. The reaction mixture was cooled to −20° C. The solution of $NaPF_6$ (0.89 g, 5.30 mmol) in $H_2O$ and acetone (10 mL) was added to the reaction mixture and stirred at −20° C. for 30 min. The mixture was slowly warmed to room temperature and stirred for 2 h. Acetone was removed under vacuum. The solid was filtered, washed with water and purified by flash column chromatography (DCM:Methanol=1:0-10:1) to afford the desired compound BrTPO (533 mg, 84%). $^1$H NMR (400 MHz, DMSO) δ 7.85 (d, J=8.6 Hz, 2H), 7.68-7.61 (m, 6H), 7.59-7.52 (m, 6H), 7.52-7.41 (m, 5H). $^{13}$C NMR (101 MHz, DMSO) δ 170.17, 158.03, 147.10, 132.63, 131.81, 131.29, 131.21, 131.11, 130.79, 130.50, 130.31, 129.43, 129.38, 129.18, 127.15, 125.57, 124.07, 122.58, 119.31.

Example 8

Synthesis and Characterization of 3MOAcTPO

An exemplary reaction scheme for preparing 3MOAcTP is as provided below:

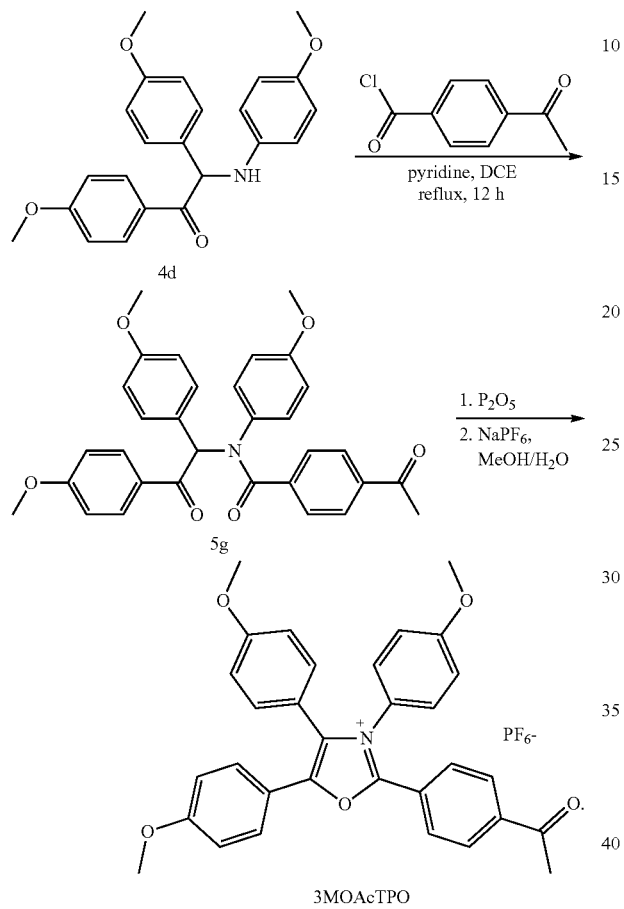

Synthesis of Compound 5g 4-acetylbenzoyl chloride (1.58 g, 8.63 mmol) was added to a solution of 4d (2.17 g, 5.76 mmol) and pyridine (1.36 mL, 17.28 mmol) in 1, 2-dichloroethane (30 mL) and refluxed under nitrogen for 12 h. The reaction mixture was cooled to room temperature and washed with $Na_2CO_3$ solution (3×30 mL). The organic layer was dried over sodium sulfate. After evaporation of the solvent under vacuum, the residue was subjected to flash column chromatography with hexane/EA (20:1, v/v) to give white solid 5g (2.35 g, 78%). $^1$H NMR (400 MHz, $CD_2Cl_2$) δ 8.00 (d, J=8.9 Hz, 2H), 7.74 (d, j=8.4 Hz, 2H), 7.40 (d, J=8.4 Hz, 2H), 7.21 (s, 1H), 7.04 (d, J=8.7 Hz, 3H), 6.90 (d, J=8.9 Hz, 3H), 6.71 (d, J=8.8 Hz, 2H), 6.50 (d, J=6.8 Hz, 2H), 3.83 (s, 3H), 3.70 (s, 3H), 3.63 (s, 3H), 2.50 (s, 3H). $^{13}$C NMR (101 MHz, $CD_2Cl_2$) δ 196.56, 193.67, 169.37, 162.87, 159.03, 157.72, 140.49, 136.37, 131.95, 131.86, 131.59, 130.39, 127.73, 127.68, 126.88, 124.78, 113.37, 113.10, 112.47, 65.75, 54.84, 54.46, 25.80.

Synthesis of 3MOAcTPO

Compound 5g (0.50 g, 0.95 mmol) and phosphorus pentoxide (0.16 g, 1.15 mmol) were dissolved in dry DCM (1.0 mL) and heated under nitrogen at 180° C. for 4 h. The reaction mixture was cooled to −20° C. The solution of $NaPF_6$ (0.80 g, 4.75 mmol) in $H_2O$ and acetone (10 mL) was added to the reaction mixture and stirred at −20° C. for 30 min. The mixture was slowly warmed to room temperature and stirred for 2 h. Acetone was removed under vacuum. The solid was filtered, washed with water and purified by flash column chromatography (DCM:Methanol=1:0-10:1) to afford the desired compound 3MOAcTPO (383 mg, 62%). $^1$H NMR (400 MHz, Acetone) δ 8.12 (d, J=8.7 Hz, 2H), 7.93 (d, J=8.7 Hz, 2H), 7.63 (d, J=7.0 Hz, 2H), 7.61 (d, J=7.0 Hz, 2H), 7.41 (d, J=8.8 Hz, 2H), 7.11 (d, J=9.0 Hz, 2H), 7.04 (d, J=7.9 Hz, 2H), 7.02 (d, J=7.7 Hz, 2H), 3.84 (s, 3H), 3.83 (s, 3H), 3.80 (s, 3H), 2.62 (s, 3H). $^{13}$C NMR (101 MHz, Acetone) δ 196.12, 161.43, 161.38, 161.22, 157.25, 148.60, 140.33, 132.16, 129.48, 129.35, 128.19, 128.08, 127.36, 123.37, 123.31, 116.10, 114.96, 114.26, 114.16, 114.01, 54.58, 54.34, 54.20, 25.30.

Figure 25:
FIG. 25 depicts fluorescent photographs of 3MOAcTPO in THF/H$_2$O mixtures with different $f_{THF}$ taken under 365 nm UV irradiation (concentration: 10μ).
Figure 26:
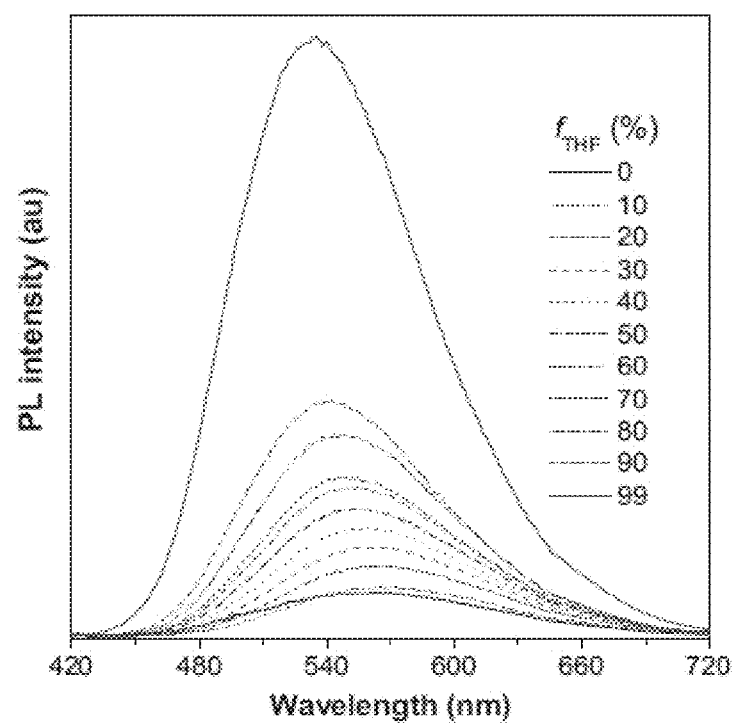
FIG. 26 depicts PL spectra of 3MOAcTPO in THF/H$_2$O mixtures with different THF fractions ($f_{THF}$) (excitation at 400 nm).
Figure 27:
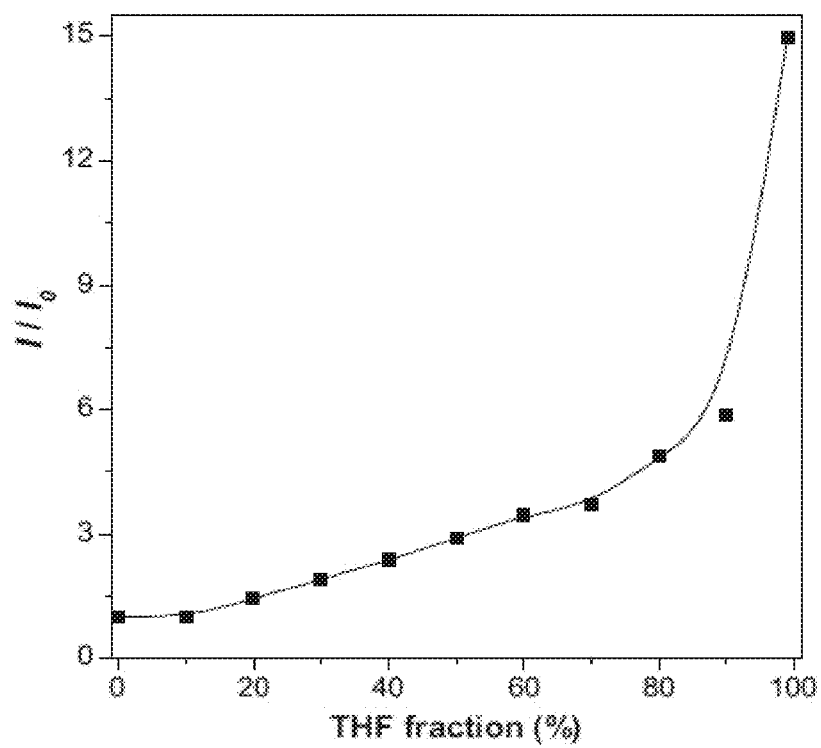
FIG. 27 depicts a plot of relative PL intensity ($I/I_0$) versus the composition of the THF/H$_2$O mixtures of 3MOAcTPO ($I_0$=PL intensity in pure THF).
Figure 28:
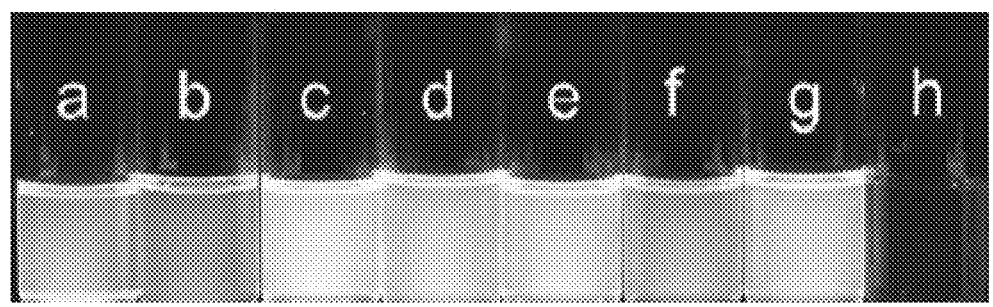
FIG. 28 depicts fluorescent photographs of 3MOAcTPO in different solvents taken under 365 nm UV irradiation, a: Hexane, b: Toluene, c: CHCl$_3$, d: Acetone, e: THF, f: EtOH, g: DMSO, and h: H$_2$O.
Figure 29:
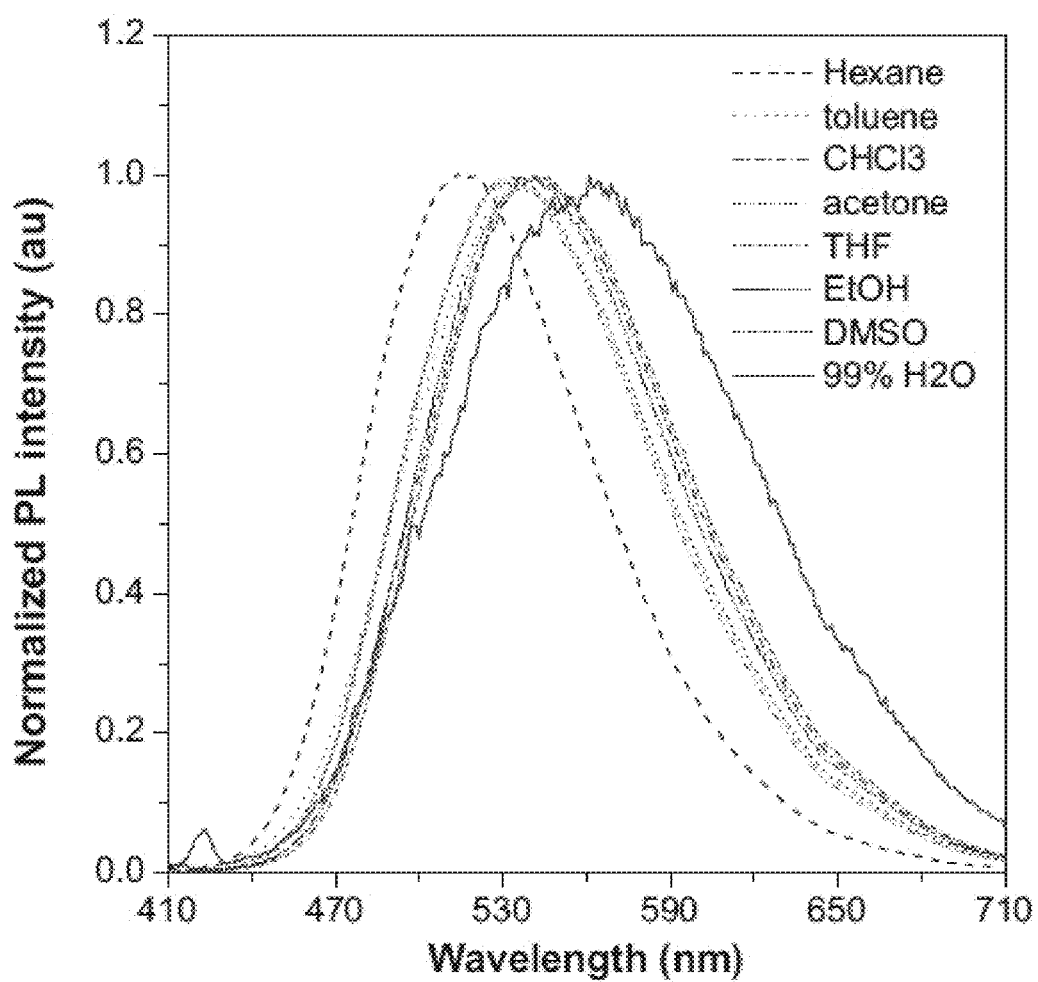
FIG. 29 depicts PL spectra of 3MOAcTPO in different solvents (excitation wavelength 370 nm, [3MOAcTPO]=10 μM).
Figure 30:
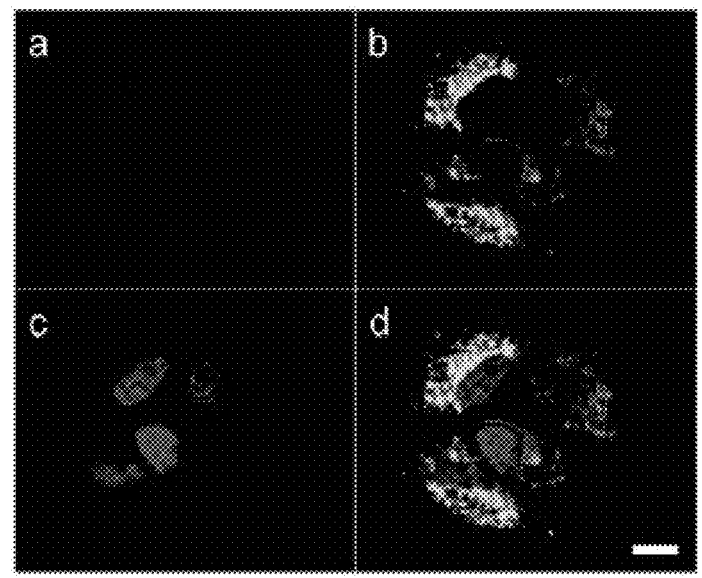
FIG. 30 depicts (a) fluorescence images of the Hela cells stained with 4MOTPO ($E_{ex}$=405 nm, $E_{em}$=440-490 nm); (b) fluorescence images of mitochondria with MitoTracker® Green FM staining ($E_{ex}$=488 nm, $E_{em}$=510-570 nm), (c) fluorescence images of nucleus with NucRed® Live staining Live ($E_{ex}$=633 nm, $E_{em}$=640-700 nm), and (d) merged image of (a), (b), and (c). Scale bar: 10 μm. Objective: 63×.
Figure 31:
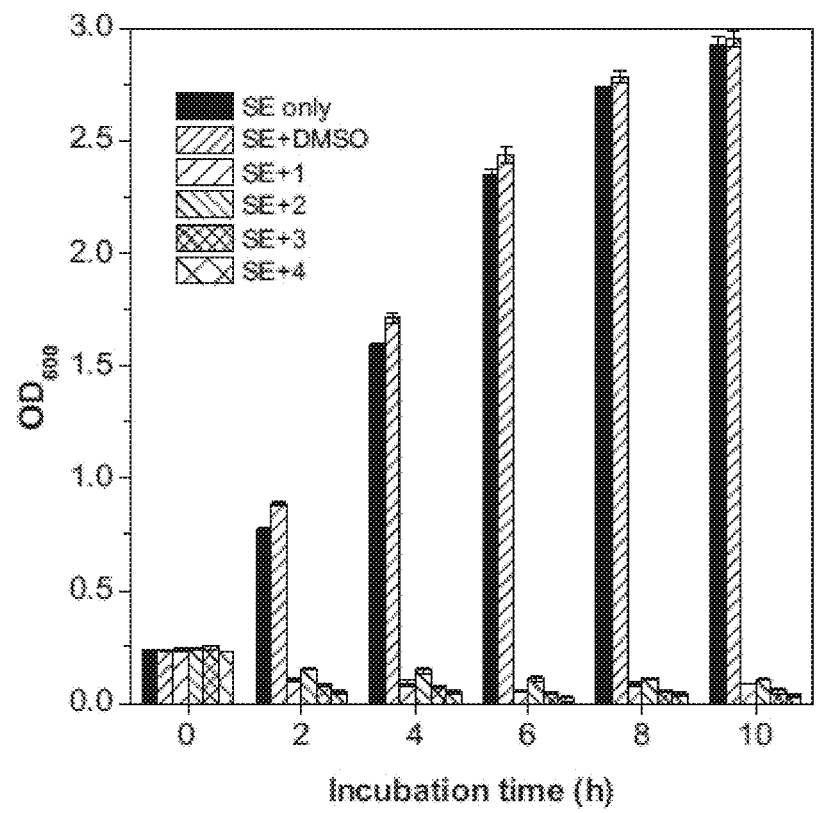
FIG. 31 depicts optical density change of SE incubated in different dyes with different incubation times (concentration: $10 \times 10^{-6}$ M. 1% DMSO. 1=1MOTPO; 2=2MOTPO; 3=3MOTPO; 4-4MOTPO).
Figure 32A:
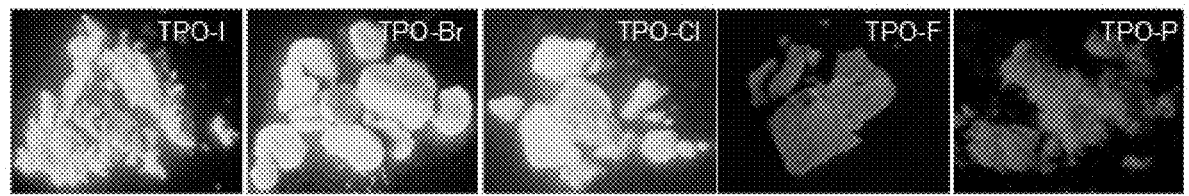
FIG. 32 depicts (a) fluorescent photographs taken under 365 nm UV irradiation of TPO-I, TPO-Br, TPO-Cl, TPO-F, and TPO-P in the solid state, (b) PL spectra of TPO-I, TPO-Br, TPO-Cl, TPO-F, and TPO-P in the solid state, (c) graph showing time-resolved PL decay of TPO-I (@ 559 nm) and TPO-Br (@ 549 nm), and (d) graph showing time-resolved PL decay of TPO-Cl (@435 nm), TPO-F (@420 nm), and TPO-P (@ 422 nm) in the solid state.
Figure 32B:
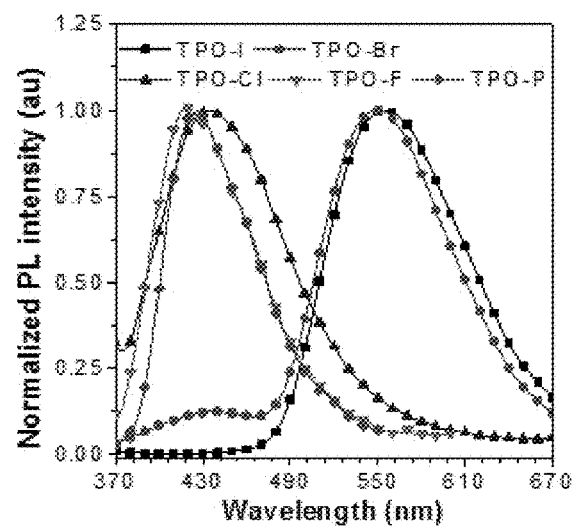
Figure 32C:
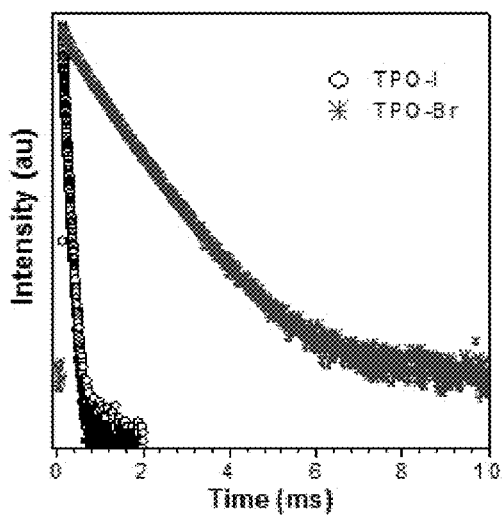
Figure 32D:
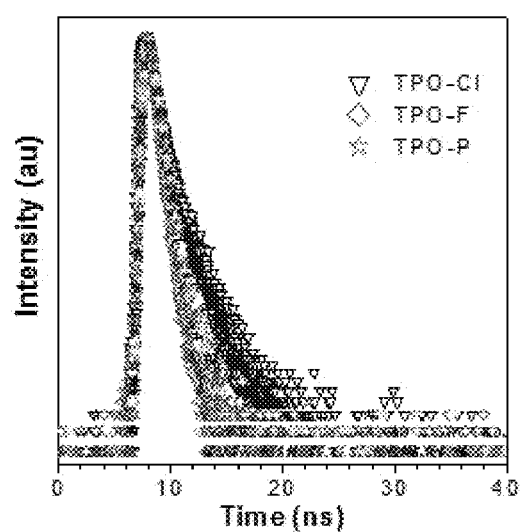

FIG. 25 depicts fluorescent photographs of 3MOAcTPO in $THF/H_2O$ mixtures with different fTHF taken under 365 nm UV irradiation (concentration: 10 μ). FIG. 26 depicts PL spectra of 3MOAcTPO in $THF/H_2O$ mixtures with different THF fractions (fTHF) (excitation at 400 nm). FIG. 27 depicts a plot of relative PL intensity (I/I0) versus the composition of the $THF/H_2O$ mixtures of 3MOAcTPO (I0=PL intensity in pure THF). FIG. 28 depicts fluorescent photographs of 3MOAcTPO in different solvents taken under 365 nm UV irradiation, a: Hexane, b: Toluene, c: $CHCl_3$, d: Acetone, e: THF, f: EtOH, g: DMSO, h: $H_2O$. FIG. 29 depicts PL spectra of 3MOAcTPO in different solvents (excitation wavelength 370 nm, [3MOAcTPO]=10 μM).

Example 9

Synthesis and Characterization of TPO-X and TPO-X Derivatives

An exemplary reaction scheme for preparing TPO-X is as provided below:

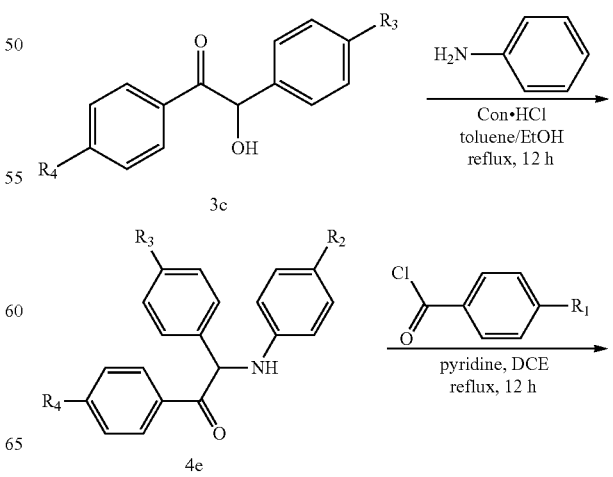

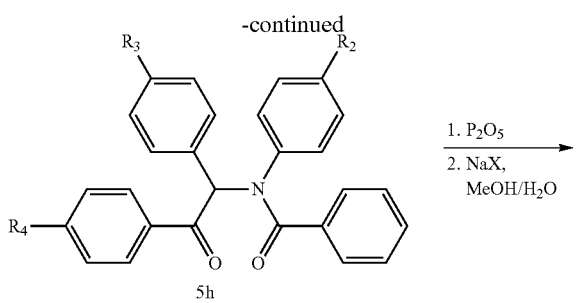

5h

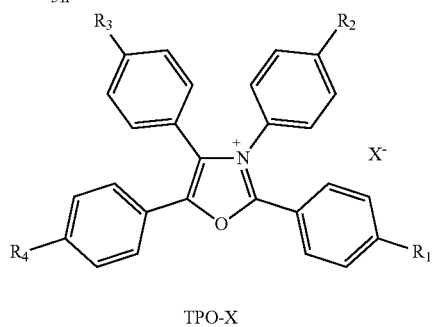

TPO-X

Compound 5h (0.50 g, 1.28 mmol) and phosphorus pentoxide (0.22 g, 1.54 mmol) were dissolved in dry dichloromethane (DCM) (1.0 mL) and the resulting mixture was heated under nitrogen at 180° C. for 4 h. After cooled to −20° C., a solution of NaX (6.40 mmol) in H$_2$O and acetone (10 mL) was added to the reaction mixture and stirred at −20° C. for 30 min. After slowly warming to room temperature and stirring for 2 h, acetone was removed under vacuum. The solid was filtered, washed with water and purified by flash column chromatography using DCM/methanol mixture (1:0-10:1, v/v) as eluent to afford the desired compound TPO-X.

Following the general procedure for the synthesis of TPO-X, TPO-I was obtained as a yellow solid (yield: 81%). $^1$H NMR (400 MHz, CD$_3$OD) δ 7.78-7.74 (m, 3H), 7.71-7.66 (m, 2H), 7.64-7.45 (m, 15H). $^{13}$C NMR (101 MHz, CD$_3$OD) δ 158.86, 147.97, 134.08, 131.25, 131.11, 130.61, 130.53, 130.33, 130.11, 129.61, 129.20, 128.66, 128.56, 128.41, 126.80, 125.64, 123.91, 122.44, 119.75. HRMS (MALDI-TOF): m/z: [M-I]$^+$ calcd for C$_{27}$H$_{20}$NO$^+$: 374.1539; found: 374.1533.

Following the general procedure for the synthesis of TPO-X, TPO-Br was obtained as a white solid (yield: 72%). $^1$H NMR (400 MHz, CD$_3$OD) δ 7.80-7.73 (m, 3H), 7.71-7.66 (m, 2H), 7.65-7.43 (m, 15H). $^{13}$C NMR (101 MHz, CD$_3$OD) δ 158.83, 147.94, 134.06, 131.23, 131.08, 130.58, 130.50, 130.31, 130.08, 129.59, 129.17, 128.64, 128.53, 128.39, 126.77, 125.62, 123.88, 122.42, 119.72. HRMS (MALDI-TOF): m/z: [M-Br]$^+$ calcd for C$_{27}$H$_{20}$NO$^+$: 374.1539; found: 374.1557.

Following the general procedure for the synthesis of TPO-X, TPO-Cl was obtained as a white solid (yield: 35%). $^1$H NMR (400 MHz, CD$_3$OD) δ 7.78-7.75 (m, 3H), 7.71-7.66 (m, 2H), 7.64-7.44 (m, 15H). $^{13}$C NMR (101 MHz, CD$_3$OD) δ 158.05, 147.06, 133.34, 130.35, 130.32, 129.73, 129.65, 129.54, 129.21, 128.85, 128.22, 127.87, 127.77, 127.61, 125.85, 124.65, 122.96, 121.52, 118.79. HRMS (MALDI-TOF): m/z: [M-Cl]$^+$ calcd for C$_{27}$H$_{20}$NO$^+$: 374.1539; found: 374.1579.

Following the general procedure for the synthesis of TPO-X, TPO-F was obtained as a white solid (yield: 18%). $^1$H NMR (400 MHz, CD$_3$OD) δ 7.81-7.72 (m, 3H), 7.69-7.66 (m, 2H), 7.64-7.41 (m, 15H). $^{13}$C NMR (101 MHz, CD$_3$OD) δ 158.95, 148.06, 134.18, 131.34, 131.20, 130.70, 130.62, 130.43, 130.20, 129.71, 129.29, 128.75, 128.65, 128.51, 126.89, 125.74, 124.00, 122.54, 119.84. HRMS (MALDI-TOF): m/z: [M-F]$^+$ calcd for C$_{27}$H$_{20}$NO$^+$: 374.1539; found: 374.1530.

Example 10

4MOTPO as Bioprobe

4MOTPO was tested in living HeLa cells to test the efficacy of the compound as a biosensor for bioimaging. Cells were incubated with 4MOTPO for 60 min at 37° C. and then washed and incubated with MitoTracker® Green FM and NucRed® Live for 10 min, followed by further washing. FIGS. 30A-30D show the intracellular distribution of 4MOTPO in Hela cells revealed by confocal microscopy. An intense blue fluorescence was observed in the cellular cytoplasms, demonstrating the great potential of 4MOTPO as an fluorescent probe for biological imaging. Control experiments using commercial available MitoTracker® Green FM and NucRed® indicated that 4MOTPO can accumulate in mitochondria.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A compound, wherein the compound is selected from the group consisting of:

1MOTPO

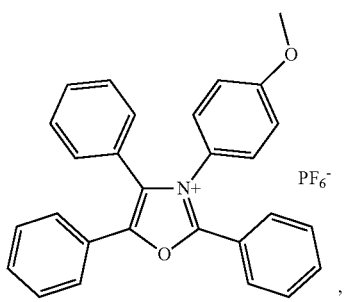

,

3MOTPO

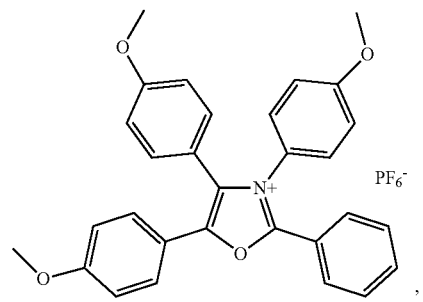

,

4MOTPO

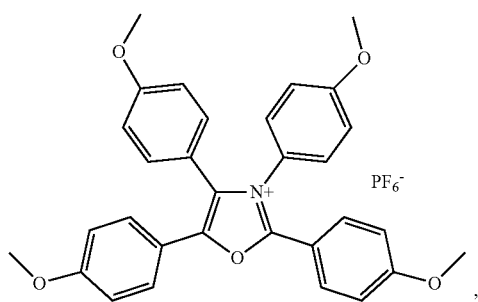

TPT-Br

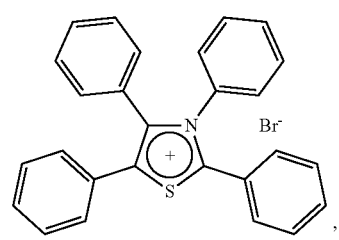

TriPI-I

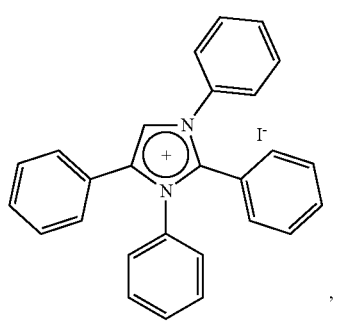

TriPI-Br

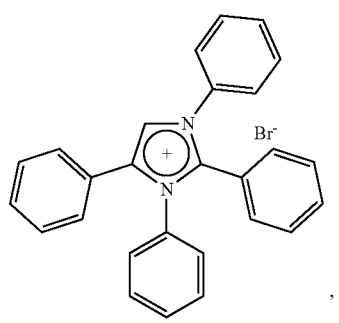

TriPT-I

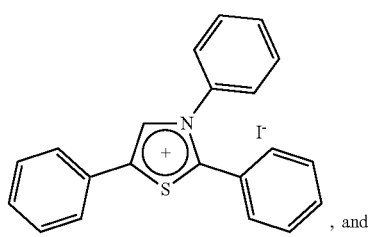
, and

TriPT-Br

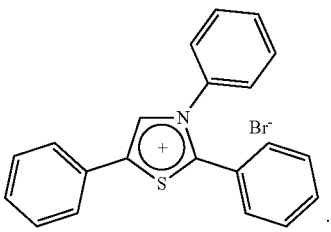

2. The compound of claim 1, wherein the compound is water soluble.

3. The compound of claim 1, wherein the compound has fluorescence properties when in a solid state.

4. The compound of claim 1, wherein the compound has at least one of fluorescence and phosphorescence properties when in a solid state.

5. The compound of claim 4, wherein the compound provides white light emission in thin films.

6. A polymer comprising the compound of claim 5 as an additive, wherein the polymer exhibits white light emission.

7. The polymer of claim 6, wherein the polymer is suitable for use in 3D printing.

8. The compound of claim 1, wherein the compound has a donor group and an acceptor group.

9. A compound, wherein the compound is selected from the group consisting of:

1MOTPO

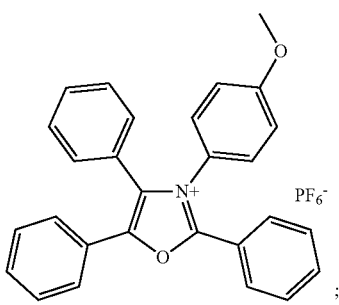
;

3MOTPO

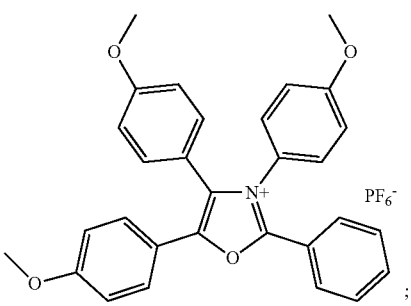
;

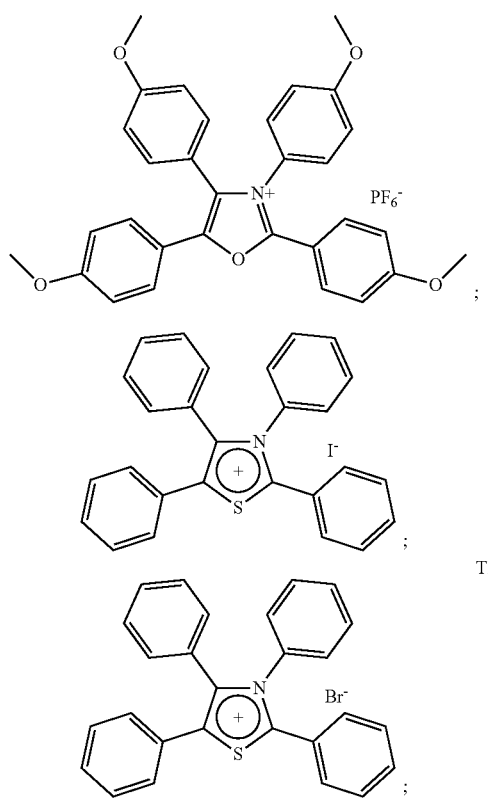
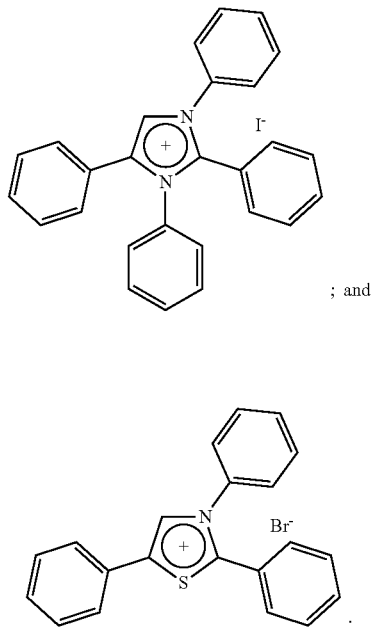
10. The compound according to claim 9, wherein the compound is water soluble.
11. The compound according to claim 9, wherein the compound has a donor group and an acceptor group.
* * * * *